United States Patent [19]

Tsushima et al.

[11] 4,068,071

[45] Jan. 10, 1978

[54] PROCESS FOR PRODUCING 6-AMINOPENICILLANIC ACID OR 7-AMINOCEPHALOSPORANIC ACID DERIVATIVES

[75] Inventors: Susumu Tsushima; Norichika Matsumoto; Mitsuo Numata, all of Osaka, Japan

[73] Assignee: Takeda Chemical Industries, Ltd., Osaka, Japan

[21] Appl. No.: 699,053

[22] Filed: June 23, 1976

Related U.S. Application Data

[63] Continuation of Ser. No. 536,916, Dec. 27, 1974, abandoned.

[30] Foreign Application Priority Data

Dec. 28, 1973 Japan .................................... 48-3181

[51] Int. Cl.$^2$ ................... C07D 501/02; C07D 499/42

[52] U.S. Cl. ........................................ 544/19; 544/26; 260/306.7 C; 260/239.1

[58] Field of Search ...................... 260/243 C, 306.7 C

[56] References Cited

U.S. PATENT DOCUMENTS 3,875,151  4/1975  Fechtig et al. ................... 260/243 C Primary Examiner—Nicholas S. Rizzo
Attorney, Agent, or Firm—Wenderoth, Lind & Ponack

[57] ABSTRACT

A derivative of 6-aminopenicillanic acid or 7-aminocephalosporanic acid is produced by a process which comprises disulfidizing a 6-thioacylaminopenicillanic acid or 7-thioacylaminocephalosporanic acid compound to obtain a corresponding disulfide compound, and then solvolyzing the disulfide compound. The process is novel and industrially feasible for producing the amino compound, which is not accompanied by "reconversion reaction".

55 Claims, No Drawings

PROCESS FOR PRODUCING 6-AMINOPENICILLANIC ACID OR 7-AMINOCEPHALOSPORANIC ACID DERIVATIVES

This application is a continuation of Ser. No. 536,916, filed Dec. 27, 1974, now abandoned.

The present invention relates to a process for producing amino compounds, more particularly to a novel and industrially feasible process for producing derivatives of 6-aminopenicillanic acid or 7-aminocephalosporanic acid of the following general formula (I), which are useful as intermediates for the synthesis of a variety of synthetic penicillins and cephalosporins;

$$H_2N - A \qquad (I)$$

wherein A is the residue of a 3-cephem or penam compound.

The process of the present invention, by which the above object amino compound (I) can be produced, comprises reacting a compound of the general formula (III)

wherein $R^1$ is an organic residue and A has the same meaning as above with a disulfidizing agent, to obtain an unsymmetrical disulfide compound of the general formula (II)

wherein $R^2$ represents substituted mercapto group and $R^1$ and A have the same meaning as above, and then, solvolyzing the compound (II).

The reactions involved in the present process are shown in the following schema;

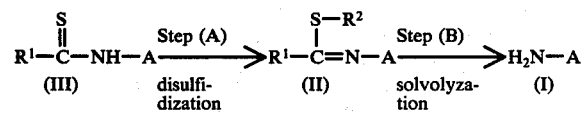

wherein A, $R^1$ and $R^2$ have the same meaning as above.

Heretofore, 6-aminopenicillanic and 7-aminocephalosporanic acid compounds (I) have been produced, for example, by the method comprising halogenating penicillin G or cephalosporin C to obtain the corresponding iminohalide, then reacting the imino-halide further with an alcohol to obtain an imino-ether compound and finally solvolyzing the imino-ether compound (Japanese Patent Publications No.13862/1966, No.27391/1969, No.40899/1970, etc.). However, known also is the fact that a "reconversion" reaction, which reproduces the starting acylamido compound from the iminoether compound, takes places as a side reaction in the course of said solvolysis (Japanese Patent Application Laid Open No.62792/1973, German Patent Application No.P 2258079.6). Further, in these methods the imino-etherification reaction must be carried out at an extremely low temperature, or specific alcohols must be employed as solvents for said solvolysis, in order to obtain the object compound in good yield.

Previously, as a means for cleavage of the acyl group of 7-acylaminocephalosporanic acid derivatives, which is not accompanied with such reconversion reaction as above, some of the present inventors developed a process involving the route via the thioacylamido-compound (Japanese Patent Application Laid Open No.34898/1973; Japanese Patent Application No.56235/1972 and No.66527/1972 German Patent Application No.P 2244620.4). However, this process is also accompanied with such drawback as troublesome handling of intermediates, because in this process the intermediate thioacylamido compound must be isolated or separated prior to the next reaction step, and in this process so-called one-batch procedure starting from the corresponding acylamido compound can not be applied. Thus, these known methods for the production of the amino compound (I) are not satisfactory from an industrial point of view such as yield, handling of intermediates, reaction temperature and kind of solvents used for said solvolysis.

Under these circumstances, the present inventors have made extensive studies for developing a novel and advantageous route for the production of the amino compound (I).

As the result of the studies, the present inventors have quite unexpectedly found out that a thioacylamido compound (III) is disulfidized with a disulfidizing agent to give a corresponding novel unsymmetrical disulfide compound (II), and the disulfide compound (II) is easily solvolized, even by readily available alcohol from an industrial point of view, such as methanol, to give an amino compound (I) at not so low a temperature, in good yield and without any substantial reconversion reaction. Further, it has also been found out that the compound (III) is employable as a starting compound of the reaction of Step (A) without prior isolation or purification thereof. As the result of these factors, the object amino compound (I) is produced in a good yield in this process.

The present invention has been accomplished on the basis of these findings. Thus, according to the present process, the object amino compound (I) can be easily produced in good yield by simple procedure and therefore the present process is remarkably feasible, effective and advantageous from an industrial point of view.

Namely, the principal and essential object of the present invention is to provide a novel and industrially feasible process for producing the amino compound (I), and this object can be attained by the process described in detail hereinafter.

In the above general formula, the organic residue represented by $R^1$ is a group capable of forming a thioacyl group with an adjacent thiocarbonyl group, which is derived from an acylamido group in 6-position of a penicillin derivative or 7-position of cephalosporin derivative by eliminating the -CONH- group. Among such organic residues are included those whose functional group, such as amino or/and carboxy, have been suitably protected. As the typical examples of those organic residues, there may be phenyl, thienylmethyl, benzyl, phenoxymethyl or 4-amino-4-carboxybutyl group whose amino or/and carboxy group may be protected. Among the above, benzyl or 4-amino-4-carboxybutyl group whose amino or/and carboxy group may be protected is preferable as the organic residue $R^1$.

As the protective group for amino group, there may be mentioned, among others, lower acyl (e.g. acetyl, propionyl), benzoyl, phenylacetyl, phenoxyacetyl, benzyloxycarbonyl, phthaloyl, isobornyloxycarbonyl, pivaloyl, p-(t-butyl)benzoyl, p-toluenesulfonyl, p-(t-butyl)benzenesulfonyl, camphorsulfonyl, etc.

Among the above, phthaloyl, isobornyloxycarbonyl, p-(t-butyl)benzoyl or p-(t-butyl)benzenesulfonyl is preferable as the protective group for free amino group.

The residue of penam compound which is represented by A is a penicillin moiety derived by eliminating the 6-acylamino group thereof, which is represented by the formula:

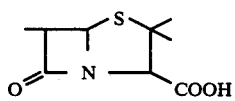

(V)

or a group corresponding to (V) whose carboxy function has been previously protected. As the residue of 3-cephem compound, use is made of a cephalosporin moiety derived by eliminating the 7-acylamino group thereof, which is represented by the general formula:

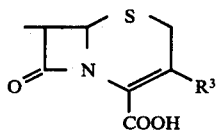

(VI)

wherein $R^3$ is a group which does not take part in the present reaction, or a group corresponding to (VI) whose carboxy function has been previously protected. The group which does not take part in the present reaction is a group which is not affected by the reaction of this invention. As typical examples of the group represented by $R^3$, there may be mentioned, among others, lower alkyl (e.g. methyl, ethyl, propyl); lower alkoxy methyl (e.g. methoxymethyl, ethoxymethyl, propoxymethyl); lower acyloxy methyl (e.g. acetoxymethyl, propionyloxymethyl); a group represented by $-CH_2SR^4$, in which $R^4$ stands for lower alkyl (e.g. methyl, ethyl or propyl) or a nitrogen-containing heterocyclic group containing not less than one nitrogen atom which may be in the oxide form or, in addition to a nitrogen atom or nitrogen atoms, such other atoms as oxygen or/and sulfur atoms. The nitrogen-containing heterocyclic group desirably has 1 to 4 hetero atoms selected from the group consisting of nitrogen, oxygen and sulfur atoms in its heterocyclic ring, and the ring may be 5 or 6 membered.

As such nitrogen-containing heterocyclic group, there may be mentioned, among others, pyridyl, N-oxide-pyridyl, pyrimidyl, pyridazinyl, N-oxide-pyridazinyl, pyrazolyl, thiazolyl, thiadiazolyl such as 1,2,3-thiadiazolyl, 1,2,4-thiadiazolyl, 1,3,4-thiadiazolyl or 1,2,5-thiadiazolyl, oxadiazolyl such as 1,2,3-oxadiazolyl, 1,2,4-oxadiazolyl, 1,3,4-oxadiazolyl or 1,2,5-oxadiazolyl, triazolyl such as 1,2,3-triazolyl or 1,2,4-triazolyl, tetrazolyl such as 1H-tetrazolyl or 2H-tetrazolyl and others. Each of these nitrogen-containing heterocyclic groups may be further substituted in its optional position by a substituent such as, for example, a monovalent group, for example, lower alkyls having 1 to 4 carbon atoms such as methyl, ethyl, trifluoromethyl, propyl, isopropyl, butyl, isobutyl, etc.; lower alkoxyls having 1 to 4 carbon atoms such as methoxy, ethoxy, propoxy, isopropoxy, butoxy, etc.; halogens such as chlorine, bromine, etc.; amino; mercapto; hydroxyl; carbamoyl; or carboxy group. As additional examples of the substituents of the heterocyclic group, there may also be mentioned, among others, monovalent group, for example, a substituted lower alkyl group such as substituted methyl, ethyl or propyl, a substituted mercapto group or a mono- or di-substituted amino group. The substituents of the substituted lower alkyl group may be hydroxyl, mercapto, amino, morpholino, carboxy, sulfo, carbamoyl, alkoxycarbonyl, mono- or di-lower alkylcarbamoyl, alkoxy, alkylthio, alkylsulfonyl, acyloxy or morpholinocarbonyl group, etc. In the substituents of the substituted lower alkyl group, the alkyl group is exemplified by methyl, ethyl or isopropyl, the alkoxy group is exemplified by methoxy, ethoxy, propoxy, butoxy, isobutoxy, hexyloxy, octyloxy, decyloxy or dodecyloxy; the acyloxy is exemplified by acetoxy, propionyloxy, valeryloxy, caproyloxy, benzoyloxy, phenylacetoxy. The substituents of the substituted mercapto group may be the same lower alkyl group or the same substituted lower alkyl group as mentioned above. The substituents of the mono- or di-substituted amino group may be carboxy, carbamoyl, or the same lower alkyl, alkoxy-carbonyl, lower alkylcarbamoyl or substituted lower alkyl group as mentioned above. As the substituents of the heterocyclic group mentioned above specifically, use may be made of, for example, a substituted lower alkyl group such as carboxymethyl, an N-lower alkylcarbamoylmethyl (e.g. N,N-dimethylcarbamoylmethyl), a hydroxy-lower alkyl (e.g. hydroxymethyl, 2-hydroxyethyl), an acyloxy-lower alkyl (e.g. acetoxymethyl, 2-acetoxyethyl), an alkoxy-carbonylmethyl (e.g. methoxycarbonylmethyl, hexyloxycarbonyl-methyl, octyloxycarbonylmethyl), methylthiomethyl, methylsulfonylmethyl, an N-lower alkylamino-lower alkyl (e.g. N,N-dimethylaminomethyl, N,N-dimethylaminoethyl), morpholinomethyl, etc., mono- or di-substituted amino groups such as a lower alkylamino (e.g. methylamino), a sulfo-lower alkylamino (e.g. 2-sulfo-ethylamino), a hydroxy-lower alkylamino (e.g. hydroxyethylamino), a lower alkylamino-lower alkylamino (e.g. 2-dimethylamino-ethylamino, a lower alkoxycarbonylamino(e.g. methoxycarbonylamino), etc., a substituted mercapto group such as methylthio, 2-hydroxyethylthio, 2-acyloxyethylthio (e.g. 2-acetoxyethylthio, 2-phenyl-acetoxyethylthio, 2-caproyloxyethylthio), carboxymethylthio, an alkoxycarbonyl-methylthio (e.g. methoxycarbonyl-methylthio, hexyloxycarbonyl-methylthio), a N-lower alkylcarbamoyl-methylthio(e.g. N,N-dimethylcarbamoyl-methylthio), an N-lower alkylamino-lower alkylthio (e.g. 2-N,N-dimethylaminoethylthio), morpholinocarbonyl-methylthio, 2-sulfoethylthio, etc.

The group represented by $R^3$ also stands for an iminomethyl group of the general formula (VII)

(VII)

wherein $R^5$ is an unsubstituted or substituted alkyl group. As examples of the unsubstituted or substituted alkyl represented by $R^5$, there may be mentioned, among others, straight-chain, oranched or cyclic alkyl groups having 1 to 6 carbon atoms (e.g. methyl, ethyl, propyl, isopropyl, n-butyl, i-butyl, sec-butyl, t-butyl, pentyl, heptyl, hexyl, cyclopentyl, cyclohexyl, etc.) and the said alkyl groups having 1 to 6 carbon atoms substituted by alkenyl, aryl, 5 to 6 membered heterocyclic group having 1 to 2 hetero atoms selected from the group consisting of nitrogen, oxygen and sulfur atom, carboxy or primary to quarternary amino groups (e.g. benzyl, furfuryl, 2-thienylmethyl, 3-thienylmethyl, allyl, tetrahydrofurfuryl, 2-pyridylmethyl, 3-pyridylmethyl, 4-pyridylmethyl, 2-pyridylethyl, 3-pyridylethyl, 4-pyridylethyl, carboxymethyl (-CH$_2$COOH), β-dimethylaminoethyl, β-pyrrolidinoethyl, β-piperidinoethyl, β-cycanoethyl, pyridinium methyl, β-morpholinoethyl, γ-morpholinopropyl, ect.)

Among the groups represented by the formula —CH$_2$SR$^4$, a group wherein R$^4$ is an unsubstituted or substituted nitrogen-containing heterocyclic group is preferable. Further, among the unsubstituted or substituted nitrogen-containing heterocyclic group, tetrazolyl, oxadiazolyl and thiadiazolyl groups are more preferable. As the protective group for the carboxy group of said organic residue R$^1$ or for the carboxy group of the residue of a 3-cephem or penam compound which is represented by A, there may be employed, among others, lower straight or branched alkyl having 1 to 6 carbon atoms (e.g. methyl, ethyl, tert-butyl, tert-amyl), aralkyl unsubstituted or substituted by nitro or lower alkoxy (e.g. benzyl, p-nitrobenzyl, p-methoxybenzyl), lower acyl (e.g. acetyl, propionyl), benzhydryl, 1-indanyl, phenacyl, phenyl, p-nitrophenyl, lower alkoxy alkyl (e.g. methoxymethyl, ethoxymethyl), acyloxy lower alkyl (e.g. benzyloxymethyl, acetoxymethyl), pivaloyloxymethyl, β-methylsulfonylethyl, methylthiomethyl, trityl, β, β, β-trichloroethyl, silyl groups (e.g. di or trilower alkylsilyl group such as trimethylsilyl, dimethylsilyl), phosphorus trichloride, etc. Further, said coarboxy groups may each be employed in the form of an inorganic or organic salt with, for example, an alkali metal or alkaline earth metal, e.g. sodium, potassium or magnesium or the like, or any of various amines. As the said protective group for carboxy group, β-methylsulfonylethyl, phosphorus trichloride and silyl groups are preferable.

As the substituted mercapto group represented by R$^2$, there may be mentioned, among others, lower alkoxycarbonylthio groups (e.g. methoxycarbonylthio, ethoxycarbonylthio, propoxycarbonylthio), halocarbonylthio groups (e.g. chlorocarbonylthio, bromocarbonylthio), lower alkylthio groups (e.g. methylthio, ethylthio, propylthio, isopropylthio, butylthio, isobutylthio, etc.), mono-, di-or trihalo lower alkylthio groups (e.g. monochloromethylthio, dichloromethylthio, trichloromethylthio, tribromomethylthio, etc.), substituted aminothio groups (e.g. mono- or di-lower alkylaminothio such as dimethylaminothio, diethylaminothio, dipropylaminothio, methylaminothio, ethylaminothio), nitrogen-containing 5 to 6 membered heterocyclic group-substituted mercapto (such as morpholinothio, etc.), halothio or halodithio (e.g. chlorothio, chlorodithio, bromothio, bromodithio), etc.

The reaction of Step (A) is carried out by reacting a compound (III) with a disulfidizing agent. This disulfidizing reaction is effected by permitting the disulfidizing agent to act upon the compound (III).

The disulfidizing agent to be employed in this reaction is a reagent which is able to react with the compound (III) to give an intermediary unsymmetrical disulfide compound (II), said reagent typically including sulfenyl halide derivatives of the general formula:

R$^2$X (VIII)

wherein X is a halogen atom and R$^2$ has the same meaning as above; isothiourea derivatives of the general formula:

wherein R$^2$ has the same meaning as above and their acid addition salts; imide derivatives of the formulas:

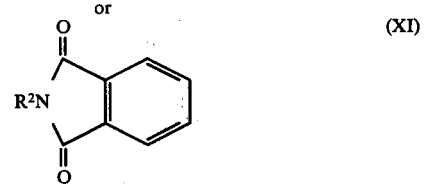

wherein R$^2$ has the same meaning as above; Bunte salts of the general formula:

wherein R$^2$ has the same meaning as above and Me represents alkali metal such as sodium or potassium. In formula (VIII), X stands for a halogen atom such as chlorine, bromine or the like.

As specific examples of said disulfidizing agent, there may be mentioned, among others, Cl$_3$CSCl, ClCH$_2$SCPl, CH$_3$OCOSCl, ClCOSCl, CH$_3$SCl, Cl$_3$CSSC$_h$ (C$_2$H$_5$)$_2$NSCl,

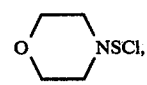

S-methylthioisothiourea, S-isobutylthioisothiourea, N-methylthiosuccinimide, N-isopropylthiosuccinimide, N-ethylthiophthalimide, N-n-butylthiophthalimide, N-propylthiophthalimide, sulfur dichloride (SCl$_2$), sulfur monochloride (S$_2$Cl$_2$), etc. Since some of these disulfidizing agents are unstable compounds, they may each be caused to form in the reaction mixture and subjected to the contemplated reaction as it occurs therein. Among the disulfidizing agent, sulfur halide, especially, sulfur chloride such as sulfur monochloride, and Cl$_3$CSCl (trichloromethanesulfenyl chloride) are preferable.

The reaction of thioacylamido compound (III) with disulfidizing agent may generally be carried out in an organic solvent and in the presence or absence of a base. Any organic solvent may be employed which will not react with the disulfidizing agent used in the reaction of Step (A). As typical examples of said solvent, there may be mentioned, among others, halogenated hydrocarbon (e.g. dichloromethane, chloroform, 1,2-dichloroethane), aromatic hydrocarbon (e.g. benzene, xylene, toluene), ester (e.g. ethyl acetate), and acetonitrile.

As the base to be used in the reaction of Step (A), inorganic or organic base may be employed. Typical examples of such inorganic base may be an alkalimetal (e.g. sodium or potassium) carbonate or bicarbonate such as potassium carbonate, sodium carbonate, sodium bicarbonate, and potassium bicarbonate. And typical examples of such organic base are pyridine, picoline, quinoline, N,N-dimethylaniline and triethylamine.

The amount of the disulfidizing agent to be used in the reaction of Step (A) is generally about 1 to 2 mole per mole of the starting compound (III).

The reaction is generally conducted at −30° C to room temperature. Some of thus-obtained unsymmetrical disulfide compounds (II) are comparatively stable and may therefore be isolated, but more generally it is preferable to subject them directly to the next solvolysis reaction of Step [B]. However, if desired, the compound (II) thus obtained may be isolated or separated by conventional means (e.g. evaporation of solvent used, column chromatography on silica gel).

The reaction of Step (B) is carried out by subjecting the resultant novel intermediate compound (II) to solvolysis reaction. The solvolysis reaction comprises reacting compound (II) with solvolysis solvent. In the reaction, the intermediate compound (II) obtained in Step (A) is preferably directly subjected, as mentioned above, to the solvolysis reaction without prior isolation. As the solvent to be used for said solvolysis, there may be mentioned alcohols including lower aliphatic alcohols having 1 to 4 carbon atoms such as methanol, ethanol, propanol, butanol, i-butanol, glycols such as ethylene glycol, propylene glycol, 1,3-butanediol, triols such as glycerin, etc.; organic carboxylic acids such as acetic acid, propionic acid, etc.; mercaptans such as methylmercaptan, ethyl mercaptan, etc.; and water to name but a few. Particularly preferred of these solvents are the alcohols, and among the alcohols straight chained monohydric ones having 1 to 3 carbon atoms such as methanol or ethanol, especially methanol is most preferable. The amount of the solvent that is theoretically required for the solvolysis is 2 mole equivalents relative to compound (II), but better results are in many cases obtained when an excess of the solvent is employed.

This solvolysis is preferably conducted in the presence of an acid. As the acid, there may be employed inorganic acids such as mineral acid (e.g. hydrochloric acid, sulfuric acid, phosphoric acid, etc.) and organic sulfonic acids such as camphorsulfonic acid, toluenesulfonic acid, benzenesulfonic acid, etc. The amount of the acid to be used is generally not less than one mole equivalent relative to compound (II). Such an acid need not be added to the reaction system of Step (B) in cases where an acid is formed with the progress of the solvolysis reaction. While the solvolysis may be effected by producing the intermediate compound (II) beforehand and then, adding a solvolysis solvent and an acid thereto, it may alternatively be carried out in such a manner that a solvolysis solvent and an acid are added prior to the production of intermediate compound (II), i.e. the reaction of Step (A), so that the addition of a disulfidizing agent will give rise to intermediate compound (II) which will then be substantially simultaneously solvolyzed.

This solvolysis reaction may be generally conducted at about −30° C to room temperature but, being an exothermic reaction, the reaction is desirably carried out under cooling.

The amino-compound (I) thus obtained may be isolated in the conventional manner. Thus, when the product has separated out as an acid addition salt corresponding to the acid used or produced from the reaction system, it may be easily isolated by mere filtration. When the carboxy group thereof has been protected with a silylating agent or phosphorus trichloride, the object amino compound (I) may be easily isolated by decomposing the protected portion of the group of the reaction product with water and adjusting the pH of the resultant mixture to its isoelectric point.

The process of this invention involving the route via the novel intermediate compound (II) is a commercially very profitable process in that, unlike the process via iminoether compound, it virtually does not entail a reconversion reaction and the reactions proceed in a single reaction vessel to give an amino-compound (I) in good yield even at mild termperatures.

The object amino compounds (I) thus produced are useful as intermediates for the synthesis of a variety of synthetic penicillins and cephalosporins. For example, by acylating the compounds (I), the cephalosporin derivatives having anti-bacterial properties and being useful as antibiotics are obtained as follows;

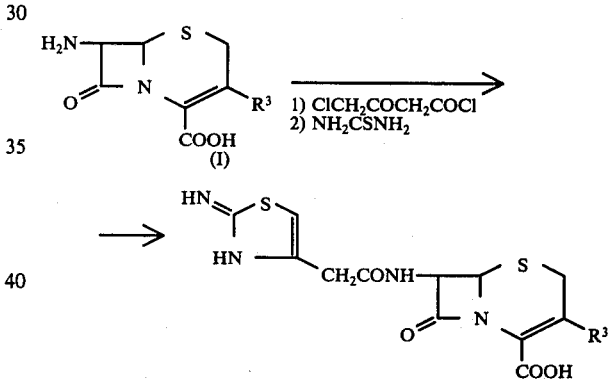

wherein $R^3$ has the same meaning as above.

The compound (III) of this invention may be produced, for example, by the procedure set forth in Japanese Patent Application Laid Open No. 34898/1973, from the corresponding acylamido compound (IV) as follows;

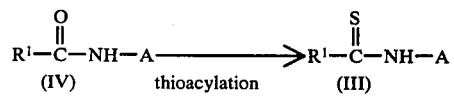

wherein $R^1$ and A have the same meaning as above.

The starting compound (IV) of this reaction can be easily produced by a fermentation process or can be easily derived from products of a fermentation process.

A compound (IV) wherein $R^3$ (of the A group) is $-CH_2SR^4$ may be produced by reacting a compound (IV) wherein $R^3$ is $-CH_2OCOCH_3$ with a corresponding mercaptan ($R^4SH$).

The thioacylation mentioned above comprises reacting compound (IV) with a sulfurizing agent such as phosphorus pentasulfide or, alternatively, by reacting compound (IV) with a halogenating agent such as phosphorus pentachloride to obtain the corresponding iminohalide compound and then reacting the product with a sulfur compound such as hydrogen sulfide, thiocarboxylic acid, thioacetamide or a phosphorous compound of the formula:

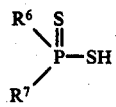

wherein $R^6$ and $R^7$ respectively represent an alkoxy (e.g. methoxy, ethoxy, propoxy) or dialkylamino group (e.g. dimethylamino).

The reaction of the compound (IV) with the sulfurizing agent is carried out in a solvent such as dichloromethane, chloroform, benzene, xylene, dioxane, ethyl acetate or carbon disulfide. This reaction is preferably conducted in the presence of a base, for example, pyridine, quinoline or N,N-dimethylaniline, generally at room temperature or under cooling with ice. The halogenating agent which is employed in the formation of the iminohalide compound may, for example, be phosphorus oxychloride, phosphorus pentachloride, phosphorus trichloride or thionyl chloride. The reaction leading to an iminohalide is generally conducted advantageously in a solvent such as chloroform or dichloromethane. This reaction is preferably carried out in the concomitant presence of an organic base such as pyridine, quinoline, N,N-dimethylaniline, triethylamine or N-methylmorpholine. As the proportion of said base, it is sufficient to add 2 to 3 equivalents based on the halogenating agent. Relative to the compound (IV), generally 1 to 2 equivalents of a halogenating agent is employed. This reaction leading to the formation of an iminohalide is preferably conducted at a temperature of about -40° C to about 30° C and it is advantageous to arrange the reaction so that it goes to completion generally in about 15 to 120 minutes.

Subsequently, to the thus-obtained reaction mixture containing the iminohalide compound, is added a sulfur compound such as hydrogen sulfide, thioacetic acid, thioacetamide or a phosphorous compound (XIII) such as dimethyl dithiophosphate, diethyl dithiophosphate, etc. The reaction with the sulfur compound proceeds within the above-mentioned temperature range to give the compound (III) in good yield. In adding the sulfur compound to the iminohalide compound, it is desirable to add simultaneously an acid acceptor such as an organic base, as mentioned in the preceding reaction. When suitable amount of hydrogen chloride and pyridine co-exists in the reaction system, the compound (III) precipitates as an adduct consisting of the compound, hydrogen chloride and pyridine (1:1:1).

In this invention said compound (III) may be subjected to the contemplated reaction of this invention either as it is in the reaction mixture obtained during its production, or after it has been previously subjected to a suitable purification process. However, the compound thus obtained is preferably subjected directly to the reaction of Step (A) without prior isolation or purification. Or the compound (III) may be subjected to the contemplated reaction in the form of an adduct to an equimolar amount each of hydrogen chloride and pyridine.

For further explanation of the present invention, the following Examples and References are given, wherein "part(s)" is based on weight unless otherwise noted and the relationship between "part(s)" and "volume part(s)" corresponds to that between "gram(s)" and "milliliter(s)".

And in the following respective Examples starting from an acylamido compound (IV), the production of the corresponding thioacylamido compound (III) was confirmed by thin layer chromatography.

Reference 1

β-methylsulfonylethyl 7-phenylacetamido-3-desacetoxy- cephalosporanate (13 parts) and pyridine (2.4 parts) were dissolved in dichloromethane (150 volume parts). At room temperature, phosphorus pentasulfide (15 parts) was added to the solution and the mixture was stirred for 5 hours.

The resultant insolubles are filtered off and the solution was washed with water, dried and concentrated. The resultant residue was chromatographed on silica gel by eluting with a mixture of dichloromethane and ether (1:4) to afford β-methylsulfonylethyl 7-phenylthioacetamido-3-desacetoxycephalosporanate (9.2 parts). Pale yellow needles (recrystallized from ethylalcohol). Melting point: 142°-144° C.

Reference 2

Phosphorus pentachloride (6.5 parts) was suspended in dichloromethane (45 volume parts), followed by the addition of pyridine (12 parts). The mixture was cooled to −10° C and β-methylsulfonylethyl 7-phenylacetamido-3-desacetoxycephalosporanate (4.38 parts) was added. After the mixture was stirred for 2 hours at the same temperature, hydrogen sulfide was bubbled through the mixture at −5 to −10° C for 3 hours.

The dichloromethane solution was poured into ice-water, and the organic layer was washed with water, dried and concentrated. The procedure yields β-methylsulfonylethyl 7-phenylthioacetamido-3-desacetoxycephalosporanate (4.26 parts). In IR and NMR spectra, the above product was in agreement with the product obtained in Reference 1.

Reference 3

In dichloromethane (2000 volume parts) was suspended phosphorous pentachloride (312 parts), and to the suspension was added pyridine (240 parts) under cooling at 0° to −5° C and stirring, followed by adding a solution of β-methylsulfonylethyl 7-phenylacetamido-3-desacetoxycephalosporanate (438 parts) dissolved in dichloromethane (2800 volume parts) over 30 minutes at the same temperature. The mixture was stirred for 1.5 hour at 0° to −5° C, and to the reaction mixture was added dimethyl dithiophosphate (640 parts) while keeping the reaction temperature under 0° C, followed by stirring for 3 hours. The reaction mixture was filtered to collect the precipitates, which were washed with dichloromethane to give the crystals (461 parts) of an adduct consisting of β-methylsulfonylethyl 7-phenylthioacetamido- 3-desacetoxycephalosporate, pyridine and hydrogen chloride (1:1:1). Melting point: 129° to 137° C (decomp.).

EXAMPLE 1

1. In dichloromethane (10 volume parts) were dissolved β-methylsulfonylethyl 7-phenylthioacetamido-3-desacetoxycephalosporanate (0.908 part) and N-ethylthiosuccinimide (0.48 part), and the solution was stirred at room temperature for 20 hours. The solvent was distilled off, and the residue was purified by column chromatography on silica gel, whereupon β-methylsulfonylethyl 7-(α-ethyldithiophenethylidene)amino-3-desacetoxycephalosporanate (0.91 part) was obtained as a principal product. Amorphous. IR(KBr disc): 1768, 1719, 1611 cm$^{-1}$ 2. The β-methylsulfonylethyl 7-(α-ethyldithiophenethylidene) amino-3-desacetoxycephalosporanate thus obtained (0.514 part) was dissolved in 1,2 -dichloroethane (4volume parts), and to the solution, under cooling with ice and stirring, 10% methanolic hydrochloric acid (0.6 volume part) was added. The mixture was stirred for 2 hours, and the resultant precipitate was recovered by filtration and recrystallized from methanol-toluene. The procedure yielded β-methylsulfonylethyl 7-amino-3-desacetoxycephalosporanate hydrochloride (0.323 part). Melting point: 187° C (decomp.). The IR spectrum of this product was in complete agreement with an authentic sample obtained by a different route of synthesis.

EXAMPLE 2

1. In dichloromethane (20 volume parts) were dissolved β-methylsulfonylethyl 7-phenylthioacetamido-3-desacetoxycephalosporanate (0.908 part) and dimethylaniline (0.363 part), and to the solution under cooling with ice and stirring, methoxycarbonylsulfenyl chloride (0.25 volume part) was added dropwise. After the drop-by-drop addition had been completed, the mixture was stirred for 10 minutes. The solvent was distilled off, and the resultant residue was purified by column chromatography on silica gel. The procedure yielded β-methylsulfonylethyl 7-(α-methoxycarbonyldithiophenethylidene) amino-3-desacetoxycephalosporanate (0.632 part). Amorphous. IR(KBr disc): 1766, 1724, 1625 cm$^{-1}$ 2. In 1,2-dichloroethane (4 volume parts) was dissolved the β-methylsulfonylethyl 7-(α-methoxycarbonyldithiophenethylidene)amino-3-desacetoxycephalosporanate thus obtained (0.544 part), and to the solution, under cooling with ice and stirring, 10% methanolic hydrochloric acid (0.6 volume part) was added. The mixture was stirred for 2 hours, and the resultant crystals were recovered by filtration. The procedure yielded β-methylsulfonylethyl 7-amino-3-desacetoxycephalosporanate hydrochloride (0.332 part). The infrared spectrum of this product was in complete agreement with that of an authentic sample.

EXAMPLE 3

1. In dichloromethane (10 volume parts) was dissolved β-methylsulfonylethyl 7-phenylthioacetamido-3-desacetoxy cephalosporanate (0.454 part), followed by the addition of pyridine (0.2 volume part). Under cooling with ice and stirring, to the solution trichloromethanesulfenyl chloride (0.1 volume part) was added, followed by stirring for 30 minutes. The reaction mixture was washed with water (10 volume parts), dried over anhydrous sodium sulfate and concentrated under reduced pressure. The procedure yielded β-methylsulfonylethyl 7-(β-trichloromethyldithiophenethylidene)amino-3-desacetoxycephalosporanate (0.601 part). IR(KBr disc): 1770, 1722, 1626 cm$^{-1}$ 2. The thus-obtained β-methylsulfonylethyl 7-(β-trichloromethyldithiophenethylidene)amino-3-desacetoxycephalosporanate (0.302 part) was dissolved in 1,2-dichloroethane (2 volume parts), and to the solution, under cooling with ice and stirring, 10% methanolic hydrochloric acid (0.3 volume part) was added. The mixture was further stirred for 2 hours. The resultant crystals were recovered by filtration. The procedure yielded β-methylsulfonylethyl 7-amino-3-desacetoxycephalosporanate hydrochloride (0.130 part), the infrared spectrum of which was in complete agreement with that of an authentic sample.

EXAMPLE 4

1. In dichloromethane (5 volume parts) was dissolved β-methylsulfonylethyl 7-phenylthioacetamido-3-desacetoxycephalosporanate (0.454 part), and to the solution, under stirring, S-isobutylthioisothiourea hydrochloride (0.21 part) and water (6 volume parts) were added.

Then, to the resultant sodium bicarbonate (0.184 part) was added, and the whole mixture was stirred for 3 hours. The resultant organic layer was purified by chromatography on silica gel to obtain β-methylsulfonylethyl 7-(α-isobutyldithiophenethylidene)amino-3-desacetoxycephalosporanate (0.35 part). Amorphous. IR(KBr disc): 1767, 1722, 1615 cm$^{-1}$ 2. The thus-obtained β-methylsulfonylethyl 7-(α-isobutyldithiophenethylidene)amino-3-desacetoxycephalosporanate (0.29 part) was dissolved in 1,2-dichloroethane (5 volume parts), and to the solution, under cooling with ice and stirring, 10% methanolic hydrochloric acid (1 volume part) was added and, the mixture was stirred for 2 hours. The resultant crystals were recovered by filtration and recrystallized from methanol-toluene. The procedure yielded β-methylsulfonylethyl 7-amino-3-desacetoxycephalosporanate hydrochloride (0.168 part).

In IR spectrum, this product was in complete agreement with the product according to Example 1.

EXAMPLE 5

1. In dichloromethane (5 volume parts) was dissolved β-methylsulfonylethyl 7-phenylthioacetamido-3-desacetoxycephalosporanate (0.454 part), followed by the addition of S-n-propylthioisothiourea hydrochloride (0.28 part). Under cooling with ice and stirring, a mixture of triethylamine (0.21 volume part) and dichloromethane (1 volume part) was added to the solution over a period of 10 minutes, and the mixture was stirred for an additional 15 minutes. The reaction mixture was washed with ice-cooled water (5 volume parts) and purified by chromatography on silica gel. The procedure yielded β-methylsulfonylethyl 7-(α-n-propyldithiophenethylidene)amino-3-desacetoxycephalosporanate (0.51 part). Amorphous. IR(KBr disc): 1764, 1722, 1625 cm$^{-1}$ 2. This product was dissolved in 1,2-dichloroethane (6 volume parts) and under cooling with ice and stirring, to the solution 10% methanolic hydrochloric acid (1.0 volume part) was added. The mixture was stirred for 2 hours, after which time the resultant crystals were recovered by filtration. The procedure yielded β-methylsulfonylethyl 7-amino-3-desacetoxycephalosporanate hydrochloride (0.282 part). The infrared spectrum of the product was in complete agreement with that of an authentic sample.

EXAMPLE 6

In dichloromethane (5 volume parts) was dissolved β-methylsulfonylethyl 7-phenylthioacetamido-3-desacetoxycephalosporanate (0.454 part), and to the solution, under cooling with ice, methanol (1 volume part) and 27% ethanolic hydrochloric acid (0.35 volume part) were added, followed by the addition of sulfur monochloride (0.1 volume part). The mixture was stirred for 30 minutes and, then, to the resultant dichloromethane was added. The resultant mixture was stirred under cooling with ice for an additional 30 minutes. The resultant precipitate was recovered by filtration to harvest crude crystals (0.361 part). This product was recrystallized from methanol-toluene. The procedure yielded β-methylsulfonylethyl 7-amino-3-desacetoxycephalosporanate hydrochloride (0.32 part). The infrared spectrum of the product was in complete agreement with that of an authentic sample. β-Methylsulfonylethyl 7-phenylacetamido-3-desacetoxycephalosporanate (i.e. reconversion product) was not detected by thin layer chromatography and IR spectrum in resultant mother liquor nor crude crystals obtained.

EXAMPLE 7

In a mixture of methanol (75 volume parts) and toluene (100 volume parts) was suspended an adduct consisting of β-methylsulfonylethyl 7-phenylthioacetamido-3-desacetoxycephalosporanate, pyridine and hydrogen chloride (28.5 parts), and to the suspension under cooling with ice and stirring, sulfur monochloride (4.5 volume parts) was added over 5 minutes. Then, toluene (300 volume parts) was added to the mixture over a period of 10 minutes, and the whole mixture was stirred for 1 hour. The resultant precipitate was recovered by filtration and washed with toluene-methanol (5:1). The procedure yielded crude crystals (17.9 parts) of β-methylsulfonylethyl 7-amino-3-desacetoxycephalosporanate hydrochloride. After recrystalization from methanol-toluene, there was obtained a pure product (16.9 parts). The infrared spectrum of the product was in complete agreement with that of an authentic sample. β-Methylsulfonylethyl 7-phenylacetamido-3-desacetoxycephalosporanate (i.e. reconversion product) was not detected by thin layer chromatography and IR spectrum in resultant mother liquor nor crude crystals obtained.

EXAMPLE 8

In toluene (57 volume parts) was suspended an adduct consisting of β-methylsulfonylethyl 7-phenylthioacetamido-3-desacetoxycephalosporanate, pyridine and hydrogen chloride (5.70 parts), and under cooling with ice, to the suspension, 10% methanolic hydrochloric acid (10 volume parts) was added. Then, to the resultant sulfur monochloride (1.0 volume part) was added under stirring, and the whole mixture was further stirred under cooling with ice for a period of 1 hour. The resultant precipitate was recovered by filtration and washed with toluene and acetone in this order. The procedure yielded crude crystals (3.4 parts) of β-methylsulfonylethyl 7-amino-3-desacetoxycephalosporanate hydrochloride. After recrystallization from methanol-toluene, there was obtained a pure product (3.2 parts). The infrared spectrum of the product was in complete agreement with that of an authentic sample.

EXAMPLE 9

In a mixture of 1,2-dichloroethane (40 volume parts) and 10% methanolic hydrochloric acid (6 volume parts) was suspended an adduct consisting of β-methylsulfonylethyl 7-phenylthioacetamido-3-desacetoxycephalosporanate, pyridine and hydrogen chloride (5.70 parts), and to the suspension, after cooling to −5° C, one of the under-mentioned reagents, $R^8SX$, was added.

After a reaction time of a few hours (e.g. 1.5 − 5 hours), the resultant crystals were recovered by filtration and recrystallized from methanol-toluene. The procedure yielded β-methylsulfonylethyl 7-amino-3-desacetoxycephalosporanate hydrochloride. The results are summarized below in the table. The infrared spectrum of the product was in complete agreement with that of an authentic sample.

| No. of Examp. | $R^8SX$ | Amount added | | Reaction time | Yield (part) | Percent yield (%) |
|---|---|---|---|---|---|---|
| 9-(1) | Cl$_3$CSCl | 1.5 | volume parts | 2 hrs. | 3.23 | 90.5 |
| 9-(2) | Cl$_3$CSSCl | 1.5 | volume parts | 4 hrs. | 2.35 | 65.8 |
| 9-(3) | ClCH$_2$SCl | 2.0 | volume parts | 5 hrs. | 1.59 | 44.5 |
| 9-(4) | $\overset{O}{\underset{\|}{CH_3OCSCl}}$ | 1.5 | parts | 5 hrs. | 1.70 | 47.6 |
| 9-(5) | S$_2$Cl$_2$ | 1.0 | volume parts | 2 hrs. | 3.32 | 93.0 |
| 9-(6) | ⟨O⟩NSCl | 1.70 | parts | 1.5 hrs. | 2.76 | 77.3 |

EXAMPLE 10

In dichloromethane (10 volume parts) was suspended 7-phenylthioacetamido-3-desacetoxycephalosporanic acid (0.348 part), and to the suspension, under cooling with ice and stirring, trichloromethanesulfenyl chloride (0.1 volume parts) was added. The mixture was stirred for 10 minutes. Under cooling with ice, methanol (5 volume parts) and concentrated hydrochloric acid (0.3 volume part) were added to the reaction mixture, and the whole mixture was stirred for 30 minutes. Following the addition of water (10 volume parts), the mixture was adjusted to pH 3.8 with aqueous ammonia and stirred for 30 minutes. The resultant precipitate was recovered by filtration, washed with dichloromethane, acetone and methanol in this order and finally dried.

The procedure yielded 7-amino-3-desacetoxycephalosporanic acid (0.195 part). In IR spectrum, this product was found in good agreement with an authentic sample obtained by a different route of synthesis.

EXAMPLE 11

1. In dichloromethane (5 volume parts) was suspended 7-phenylthioacetamido-3-desacetoxycephalosporanic acid (0.348 part) and, then, N,N-dimethylaniline (0.2 volume part) was added to the suspension. Under cooling with ice and stirring, a solution of morpholine-N-sulfenylchloride (0.154 part) in dichloromethane (1 volume part) was added dropwise to the mixture over a period of 5 minutes, and the whole mixture was further stirred for 10 minutes. The reaction mixture was then washed with water, dried and concentrated under reduced pressure. The procedure yielded 7-(α-morpholinodithiophenethylidene)amino-3-desacetoxycephalosporanic acid (0.465 part). Amorphous. IR(KBr disc): 2600 − 2100, 1772,1620 cm$^{-1}$ 2. The above product was suspended in dichloromethane (10 volume parts), and to the suspension, under cooling with ice and stirring, 10% methanolic hydrochloric acid (1 volume part) was added. The mixture was stirred for 30 minutes. Then, following the addition of water (10 volume parts), the whole mixture was adjusted to pH 3.8 with aqueous ammonia and stirred for 30 minutes. The resultant precipitate was recovered by filtration, washed with dichloromethane, acetone and methanol and dried. The procedure yielded 7-amino-3-desacetoxycephalosporanic acid (0.20 part), the infrared spectrum of which was in complete agreement with that of an authentic sample.

EXAMPLE 12

In dichloromethane (30 volume parts) was suspended 7-phenylacetamido-3-desacetoxycephalosporanic acid (1.66 parts), and to the suspension, under cooling with ice and stirring, triethylamine (0.51 part) was added. Then, to the resultant N,N-dimethylaniline (1.33 volume parts) was added, followed by the addition of dimethyldichlorosilane (0.5 volume part). The mixture was stirred under cooling with ice for 30 minutes and, then, at room temperature for 30 minutes. The resultant mixture was chilled to −20° C, and to the mixture phosphorus pentachloride (1.2 parts) was added.

The mixture was stirred at −20° to −10° C for about one hour, and to the resultant thioacetamide (0.75 part) was added at −20° C. The mixture was further stirred for 1.5 hours, after which time to the mixture, trichloromethanesulfenyl chloride (1.2 volume parts) was added dropwise. The mixture was stirred for 40 minutes and, at −20° C, to the mixture methanol (10 volume parts) was added. Then, to the resultant concentrated hydrochloric acid (1 volume part) was added, and the whole mixture was stirred for another 1 hour. Following the addition of water (10 volume parts), the mixture was adjusted to pH 3.8 with concentrated aqueous ammonia and, then, allowed to stand in the cold. The resultant precipitate was recovered by filtration, washed well with methanol, acetone and dichloromethane and dried. The procedure yielded 7-amino-3-desacetoxycephalosporanic acid (0.910 part), the infrared spectrum of which was in complete agreement with that of an authentic sample.

EXAMPLE 13

In dichloromethane (20 volume parts) was suspended 7-phenylacetamido-3-desacetoxycephalosporanic acid (1.66 parts) and, then, to the suspension N,N-dimethylaniline (1.9 volume parts) was added. The mixture was chilled to −20° C and, following the addition of phosphorus trichloride (0.262 volume part), the mixture was stirred for 20 minutes. To the mixture was added phosphorus pentachloride (1.3 parts), followed by stirring for 30 minutes, after which time, to the resultant thioacetamide (0.6 part) was added. The mixture was stirred for 45 minutes. At −20° C, N,N-dimethylaniline (1.9 volume parts) was added to the reaction mixture and, then, to the resultant trichloromethanesulfenyl chloride (1.0 volume part) was added. The mixture was stirred for 30 minutes, after which time, methanol (8 volume parts) was added to the mixture. The mixture was further stirred for 20 minutes and, with the addition of water (8 volume parts), from the mixture the resultant water layer was separated out. The water layer was adjusted to pH 3.8 with 6N sodium hydroxide and allowed to stand in the cold for 12 hours. The resultant precipitate was recovered by filtration, washed with methanol and methanol-water (3:1) in this order and dried. The procedure yielded 7-amino-3-desacetoxycephalosporanic acid (0.902 part), the infrared spectrum of which was in complete agreement with that of an authentic sample.

EXAMPLE 14

In dichloromethane (40 volume parts) was suspended N-phthaloyl-cephalosporin C (2.8 parts, and to the suspension, under cooling with ice and stirring, triethylamine (1.0 part), N,N-dimethylaniline (2,9 volume parts) and dimethyldichlorosilane (0.7 volume part) were added. The mixture was stirred for 1 hour. The reaction mixture was chilled to −20° C, and to the resultant phosphorus pentachloride (1.4 parts) was added. The mixture was stirred at the same temperature for 1.5 hours, after which time thioacetamide (0.75 parts) was added to the mixture. The whole mixture was further stirred at −20° to −15° C for 1 hour and to the resultant N,N-dimethylaniline (1.4 volume parts) was added. Then, at −20° C, trichloromethanesulfenyl chloride (1.6 volume parts) was added dropwise to the mixture. After 40 minutes' stirring, to the mixture methanol (10 volume parts) and 10% methanolic hydrochloric acid (2 volume parts) were added, followed by stirring for 30 minutes.

To the mixture was added water (10 volume parts) and the resultant was adjusted to pH 3.5 with concentrated aqueous ammonia.

The mixture was then allowed to stand and cool. The resultant crystals were recovered by filtration and washed well with methanol and dichloromethane.

The procedure yielded 7-aminocephalosporanic acid (1.0 part), the infrared spectrum of which was in complete agreement with that of an authentic sample.

EXAMPLE 15

N-phthaloyl-cephalosporin C (2.728 parts) was suspended in dichloromethane (30 volume parts) at 0° C and, then, triethylamine (1.4 volume parts) was added to the suspension. The mixture was stirred for 10 minutes, at the end of which time, to the mixture N,N-dimethylaniline (3.35 volume parts) and dimethyldichlorosilane (0.7 volume part) were added in succession. The mixture was stirred for 1 hour. The resultant mixture was chilled to −20° C, and to the resultant phosphorus pentachloride (1.40 parts) was added. After 90 minutes' stirring, to the mixture thioacetamide (1.0 part) was added and, the whole mixture was stirred at −10° C for 30 minutes. Then, methanol (10 volume parts) was slowly added to the mixture, followed by the addition of sulfur monochloride (1.0 volume part). The mixture was stirred for 10 minutes, after which to the resultant water (7 volume parts) was added. The mixture was adjusted to pH 7.5 with concentrated aqueous ammonia and, then, stirred at 0° C for 20 minutes. The resultant insolubles were filtered off and, the filtrate was adjusted to pH 3.5 with concentrated hydrochloric acid and, then, stirred at 0° C for 1 hour.

The resultant crystals were recovered by filtration, washed with dichloromethane, methanol and 75% methanol in this order and dried. The procedure yielded 7-aminocephalosporanic acid (1.020 part), the infrared spectrum of which was in complete agreement with that of an authentic sample.

EXAMPLE 16

In dichloromethane (40 volume parts) was dissolved N.N-dimethylaniline (5.32 volume parts) and, then, to the solution 7-(5-p-t-butylbenzoylamido-5-carboxyvaleramido)-3-(2-morpholinoethoxy)iminomethyl-3-cephem-4-carboxylic acid (4.62 parts) was suspended. The suspension was chilled to −10° C and, under stirring, to the suspension phosphorus trichloride (1.575 volume parts)was added. The mixture was stirred at −10° C for 1 hour, after which time it was chilled to −20° C, and to the mixture phosphorus pentachloride (2.9 parts) was added. The resultant mixture was stirred at −15 to −20° C for 2 hours, at the end of which time to the mixture thioacetamide (2.25 parts) was added, followed by stirring for one hour. To the resultant mixture methanol (20 volume parts) was slowly added dropwise at −20° C. After 30 minutes' stirring, to the resultant trichloromethanesulfenyl chloride (5.6 parts) was added and the mixture was stirred for 1 hour. Following the addition of water (20 volume parts), the mixture was extracted three times with each of water (20 volume parts).

The extracts were pooled and concentrated and, the resultant concentrate was developed on a chromatographic column of XAD-2 type resin with water as the eluent. The eluate was freeze-dried.

The procedure yielded 7-amino-3-(2-morpholinoethoxy)iminomethyl-3-cephem-4-carboxylic acid (2.12 part). IR(KBr): 1788 cm$^{-1}$
NMR(in D$_2$O): δ3.2–4.9(m, 14H), 5.20(d,J=5Hz,6-H), 5.56 (d,J=5Hz), 8.57(s, -CH=NO-).

EXAMPLE 17

In dichloromethane (25 volume parts) was suspended potassium salt of benzylpenicillin (6.0 parts) and to the suspension, under stirring at room temperature, N,N-dimethylaniline (5.2 volume parts) and dichlorodimethylsilane (1.6 volume parts) were added in succession and, the mixture was stirred for 30 minutes. Then, the mixture was chilled to −30° C and phosphorus pentachloride (3.6 parts) was added, followed by stirring for 2 hours at −30° C. Then, to the resultant thioacetamide (1.5 parts) was added and the mixture was further stirred at −40 to −25° C for 1.5 hours. Then, under stirring at −40° C, to the mixture methanol (20 volume parts) was added drop by drop in such a manner that the temperature of −30° C was not exceeded, followed by the addition of trichloromethanesulfenyl chloride (2.3 volume parts). The mixture was stirred for 30 minutes. Under stirring at −30° C to the mixture water (5 volume parts) was added and, then, to the mixture concentrated aqueous ammonia (20 volume parts) was slowly added dropwise. Then, on an icewater bath, the resultant was adjusted to pH 4.1 with ammonia water, followed by stirring for 1 hour. The resultant precipitate was recovered by filtration, washed with 50% methanol and dichloromethane and dried. The procedure yielded 6-aminopenicillanic acid (2.2 part). In IR spectrum, this product was found in good agreement with an authentic sample.

EXAMPLE 18

1. In a mixture of water (500 volume parts) and acetone (150 volume parts) was dissolved monosodium salt of cephalosporin C (47.4 parts), and the solution was adjusted to pH 9.0 with sodium carbonate. To the solution was added dropwise p-(t-butyl)benzoyl chloride (27.9 parts) over a period of 1.5 hours under cooling at 10 to 15° C and stirring, during which time the reaction system was kept at pH 9.0 with sodium carbonate. After stirring for further 1.5 hours at the same temperature, the reaction mixture was adjusted to pH 7.0 with phosphoric acid, and acetone was distilled off under reduced pressure. The residue was washed twice with ethyl acetate (400 volume parts each), and the resultant water layer was adjusted to pH 2.5 with phosphoric acid.

The resultant was extracted three times with each of ethyl acetate (600 volume parts each), and the ethyl acetate layer was dried over sodium sulfate and concentrated to dryness under reduced pressure. The procedure yielded N-[p-(t-butyl)benzoyl]cephalosporin C (40.1 parts). IR(KBr disc): 1778, 1730, 1708 cm$^{-1}$
NMR(in d$_6$-DMSO): δ1.28(9H), 1.5 – 1.9(4H), 2.01(3H), 2.10 – 2.35(2H), 3.36 and 3.61(2H,ABq), 4.37(1H), 4.68 and 4.99(2H,ABq), 5.06(1H), 5.67(1H), 7.46 and 7.82(4H, ABq), 8.41(1H), 8.79(1H).

2. In phosphate buffer solution of pH 6.4(60 volume parts) were dissolved N-[p-(t-butyl)benzoyl]cephalosporin C (5.75 parts) ,1-methyl-1H-tetrazol-t-thiol and sodium bicarbonate (2.52 parts), and the solution was adjusted to pH 6.4 with sodium bicarbonate. The solution was heated at 60° C for 14 hours in nitrogen gas stream under stirring. After cooling, the reaction mixture was adjusted to pH 2.5 with phosphoric acid and the resultant was extracted twice with each of ethyl acetate (80 volume parts). The ethyl acetate layer was dried over sodium sulfate and concentrated to dryness under reduced pressure. The procedure yielded 7-(D-5-p-t-butylbenzoylamido-5-carboxy-valeramido)-3-(1-methyltetrazol-5-yl) thiomethyl-3-cephem-4-carboxylic acid (3.82 parts).

3. In dichloromethane (20 volume parts) was suspended 7-(D-5-p-t-butylbenzoylamido-5-carboxyvaleramido)-3-(1-methyl-tetrazol-5-yl)thiamethyl-3-cephem-4-carboxylic acid (3.16 parts), and to the suspension were added triethylamine (1.2 volume parts), N,N-dimethylaniline (4.0 volume parts) and dimethyldichlorosilane (1.0 volume part) in this order, followed by stirring at 30° C for 1 hour. To the reaction mixture, which was chilled to −25° C, was added phosphorus pentachloride and the whole mixture was stirred for 1.5 hours. To the resultant was added thioacetamide (1.2 parts) at −20° C and the mixture was stirred at −10° to −15° C for 1 hour. After which time, to the reaction mixture were added slowly methanol (10 volume parts) and sulfur monochloride (1.2 volume parts) in this order. To the resultant mixture were further added water (10 volume parts) at −20° C and then the whole mixture was adjusted to pH 3.3 with ammonium bicarbonate (3.0 parts), followed by cooling with ice under stirring. The resultant crystals were recovered by filtration, washed with 50% methanol, methanol and dichloromethane in this order and dried to give slightly yellow powder. In water (10 volume parts) was suspended the powder, and the suspension was adjusted to pH 7.5 with ammonium bicarbonate under cooling with ice, followed by stirring for one hour. The insolubles were filtered off, and to the filtrate was added methanol (20 volume parts). The mixture was adjusted to pH 3.3 with diluted hydrochloric acid under cooling with ice and the resultant was stirred for one hour. The resultant crystals were recovered by filtration, washed with 50% methanol, methanol and dichloromethane in this order and dried. The procedure yielded 7-amino-3-(1-methyl-tetrazol-5-yl)thiomethyl-3-cephem-4-carboxylic acid (0.85 part). IR(KBr disc): 1795 cm$^{-1}$
NMR (in D$_2$O + NaHCO$_3$): δ 3.61 and 3.98 (ABq,J=18Hz,2-CH$_2$), 4.21(s,tetrazol —CH$_3$), 5.21(d,J=4.5Hz,6-H), 5.60(d,J=4.5Hz,7H).

EXAMPLE 19

According to a similar procedure to that of example 18-(3), from the following 7-substituted amino-3-cephem-4-carboxylic acid derivatives (i.e. starting compounds) were obtained the corresponding 7-amino-3-cephem-4-carboxylic acid derivatives (i.e. products) respectively, which are described in the following table;

separated out, and small amount of ethyl acetate remaining in the layer was distilled off under reduced pressure. To the resultant water layer was added 1-methyl-1H-tetrazol-5thiol(5.0 parts), and the mixture was adjusted to pH 5.0 with dipotassium phosphate, followed by stirring and heating at 65° C on a steambath for 4 hours. After cooling the reaction mixture was adjusted to pH 2.0 with phosphoric acid and extracted with ethyl acetate (200 volume parts). The ethyl acetate layer was dried on sodium sulfate and concentrated. To the resultant residue was added toluene to give powdery product. The product was recovered by filtration, dried and then dissolved in ethyl acetate. The resultant insolubles were filtered off and the filtrate was concentrated under reduced pressure.

To the resultant residue was added toluene to give powdery product. One more same purification procedure yielded 7-(D-5-phthalimido-5-carboxyvaleramido)-3-(1-methyltetrazol-5-yl)thiomethyl-3-cephem-4-carboxylic acid (13.0 parts). IR(KBr disc): 1778, 1717 cm$^{-1}$
NMR(in d$_6$-DMSO): δ 1.3'-2.5(m,6H), 3.63(ABq, 2-

| Ex. | Starting compound (amount used) | Product (yield) | IR: cm$^{-1}$ (KBr disc) | NMR: δ (in D$_2$O + NaHCO$_3$) |
|---|---|---|---|---|
| 19-(1) | 7-(D-5-phthalimido-5-carboxyvaleramido)-3-(5-methyl-1,3,4-thiadiazol-2-yl)thiomethyl-3-cephem-4-carboxylic acid (3.14 parts) | 7-amino-3-(5-methyl-1,3,4-thiadiazol-2-yl)thiomethyl-3-cephem-4-carboxylic acid (0.88 parts) | 4.46(ABq,J = 13Hz,3-CH$_2$),5.17(d, 1795 | 2.87(s, thiodiazol —CH$_3$),3.53 and 3.95(ABq,J = 18Hz,2-CH$_2$), 4.10 and J = 4.5Hz,6-H)5.58(d,J = 4.5Hz, 7-H) |
| 19-(2) | 7-(D-5-phthalimido-5-carboxyvaleramido)-3-(1,3,4-thiadiazol-2-yl)thiomethyl-3-cephem-4-carboxylic acid (3.0 parts) | 7-amino-3-(1,3,4-thiadiazol-2-yl)thiomethyl-3-cephem-4-carboxylic acid (0.82 part) | 1798 | 3.57 and 3.96(ABq, J = 18Hz,2-CH$_2$), 4.17 and 4.69(ABq,J = 14Hz,3-CH$_2$), 5.18(d,J = 5Hz,6-H), 5.58(d,J = 5Hz,7-H), 9.58(s,thiadiazol—H). |
| 19-(3) | 7-(D-5-phthalimido-5-carboxyvaleramido)-3-(5-methyl-1,3,4-oxadiazol-2-yl)thiomethyl-3-cephem-4-carboxylic acid (3.0 parts) | 7-amino-3-(5-methyl-1,3,4-oxaidazol-2-yl)-thiomethyl-3-cephem-4-carboxylic acid (1.01 parts) | 1798 | 2.74(s,oxadiazol—CH$_3$), 3.58 and 4.02(ABq,J = 18Hz,2-CH$_2$), 4.10 and 4.68(ABq,J = 14Hz,3-CH$_2$), 5.22(d,J = 5Hz,6-H),5.62(d, J = 5Hz,7-H). |
| 19-(4) | 7-(D-5-benzoylamido-5-carboxyvaleramido)-3-(1-methyltetrazol-5-yl)thiomethyl-3-cephem-4-carboxylic acid (2.88 parts) | 7-amino-3-(1-methyl-tetrazol-5-yl)thio-methyl-3-cephem-4-carboxylic acid (0.89 part) | | in good agreement to that of the product of Example 18 in IR and NMR spectra |

EXAMPLE 20

1. In a 10% aqueous solution of dipotassium phosphate (200 volume parts) was dissolved sodium salt of cephalosporin C (20 parts), and the solution was adjusted to pH 9.1 with tribasic potassium phosphate. To the solution were added acetone (80 volume parts) and then a solution of N-carboethoxyphthalimide (12 parts) in acetone (120 volume parts) under stirring at 22° C, followed by stirring at the same temperature for further one hour, during which time pH value of the reaction system was kept to 9.1 with tribasic potassium phosphate. The resultant reaction mixture was adjusted to pH 7 with phosphoric acid, and then, acetone was distilled off under reduced pressure. The residue was washed with ethyl acetate, adjusted to pH 2.0 with phosphoric acid and then extracted with ethyl acetate (200 volume parts).

To the ethyl acetate layer was added water (200 volume parts), and the mixture was adjusted to pH 7.0 with sodium bicarbonate under stirring. The water layer was CH$_2$), 3.93 (s,tetrazol -CH$_3$), 4.30(3-CH$_2$S-), 4.73(t,}N-CH-COO), 5.01(d,J=5Hz, 6-H), 5.62(q,J=5 and 8 Hz,7-H), 7.85

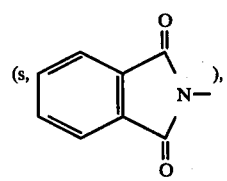

(s, ), N—

7.78(d,J=8Hz)

2. According to the similar procedure to that of Example 18-(3), from 7-(D-5-phthalimido-5-carboxyvaleramido)-3-(1-methyltetrazol-5-yl)thiomethyl-3-cephem-4-carboxylic acid (3.0 parts) was obtained 7-amino-3-(1-methyltetrazol-5-yl)thiomethyl-3-cephem-4-carboxylic acid (0.92 part). This product was in complete agreement with the product of Example 18 in IR and NMR spectra.

EXAMPLE 21

1. According to the similar procedure to that of Example 18-(1) except that p-(t-butyl)benzoylchloride was replaced with p-(t-butyl) benzenesulfonylchloride (29.4 parts) and the reaction was carried out at room temperature (about 20° C), N-[p-(t-butyl)benzenesulfonyl]-cephalosporin C was obtained from monosodium salt of cephalosporin C. IR(KBr disc): 1770, 1728, 1710, 1660 cm$^{-1}$ NMR(in d$_6$-DMSO): δ1.29(9H), 2.01(3H), 3.40 and 3.64(2H, ABq, 4.70 and 5.02(2H,ABq), 5.06(1H,d),5.64(1H,q), 7.50 and 7.68(4H, ABq), 7.94(1H,d), 8.72(1H,d).

2. According to the similar procedure to that of Example 18-(2), 7-(D-5-t-butylbenzenesulfonamido-5-carboxyvaleramido)- 3-(1-methyltetrazol-5-yl)thiomethyl-3-cephem-4-carboxylic acid (3.67 parts) was obtained from N-[p-(t-butyl)benzenesulfonyl]cephalosporin C (6.11 parts). IR(KBr disc): 1783, 1731, 1158 cm$^{-1}$ NMR(in d$_6$DMSO): δ1.27(s,9H), 1.51(4H), 2.08(2H), 3.66(2H, 2-CH$_2$), 3.92(s,3H, tetrazol —CH$_3$), 4.28(2H,3,-CH$_2$), 5.02 (d,J=5Hz,6-H), 5.60(dd,J=5 and 8Hz, 7-H), 7.51 and 7.69(4H, ABq), 7.94(d,J=8Hz,NHSO$_2$), 8.74(d,J=8Hz,CONH).

3. According to similar procedure to that of Example 18-(3), 7-amino-3-(1-methyltetrazol-5-yl)thiomethyl-3-cephem-4-carboxylic acid (0.91 part) was obtained from 7-(D-p-t-butylbenzenesulfonamide-5-carboxyvaleramido)-3-(1-methyl-tetrazol-5-yl)thiomethyl-3-cephem-4-carboxylic acid (3.43 parts). This product was in good agreement with that of Example 18 in IR and NMR spectra.

EXAMPLE 22

1. According to the similar procedure to that of Example 18-(1) except that p-(t-butyl)benzoylchloride was replaced with isobornyl chlorocarbonate (43.3 parts), and the reaction was carried out at 3° to 4° C, N-isobornyloxycarbonyl-cephalos-porin C (55.4 parts) was obtained from monosodium salt of cephalosporin C. IR(KBr disc): 1790, 1720 cm$^{-1}$ 2. According to the similar procedure to that of Example 18-(2), from N-isobornyloxycarbonyl-cephalosporin C (5.95 parts) was obtained 7-(D-5-isobornyloxycarbonylamido-5-carboxy-valeramido)-3-(1-methyl-tetrazol-5-yl)thiomethyl-3-cephem-4-carboxylic acid (3.28 parts).

3. According to the similar procedure to that of Example 18-(3), from 7-(D-5-isobornyloxycarbonyl-amido-5-carboxyvaleramido)-3-(1-methyltetrazol-5-yl)thiomethyl-3-cephem-4-carboxylic acid (3.25 parts) was obtained 7-amino-3-(1-methyltetrazol-5-yl)thiomethyl-3-cephem-4-carboxylic acid (0.92 part). This product was in good agreement with that of Example 18 in IR and NMR spectra.

EXAMPLE 23

1. A solution of N-phthaloylcephalosporin C (5.46 parts), 2-(β-hydroxyethylthio)-5-mercapto-1,3,4-thiadiazole(1.94 parts) and sodium bicarbonate (2.20 parts) in water (60 volume parts) was heated at 65° C for 4 hours. The reaction mixture was adjusted to pH 5.0 with 4N-hydrochloric acid, followed by washing with ethyl acetate.

To the resultant were added ethyl acetate (30 volume parts) and tetrahydrofuran (20 volume parts), and the mixture was adjusted to pH 2.0 with 4N-hydrochloric acid.

The resulting organic layer was washed with a saturated aqueous solution of sodium chloride, dried over magnesium sulfate and subjected to evaporation of the solvent under reduced pressure. To the resultant residue ethyl acetate (20 volume parts) and ether (30 volume parts) to give powdery substance. The resultant powdery substance was collected by filtration to give 7-(D-5- phthalimido-5-carboxyvaleramido)-3-[5-(β-hydroxyethylthio)-1,3,4-thiadiazol-2yl]thiomethyl-3-cephem-4-carboxylic acid (4.45 parts).

IR(KBr disc): (cm$^{-1}$), 1777, 1730, 1715 NMR(in d$_6$DMSO): δ1.30 to 2.40 (m,6H), 3.20 to 3.80(m,6H), 4.36(AB pattern, 2H,J=13cps), 4.75(t,1H,J=8cps), 5.05(d,1H,J=5cps), 5.64(q,1H,J=5, 9cps), 7.88(s,4H), 8.80(d,1H,J=9cps)

2. In dry dichloromethane (25 volume parts) was suspended 7-(D-5-phthalimido-5-carboxyvaleramido)-3-[5-(β-hydroxyethylthio)-1,3,4-thiadiazol-2-yl]thiomethyl-3-cephem-4-carboxylic acid (2.8 parts), and to the suspension were added triethylamine (1.4 volume parts) N,N-dimethylaniline (5.0 volume parts) and dimethyldichlorosilane (1.5 parts) in this order under cooling with ice water. Then, the mixture was stirred at 28° C for 2 hours and then chilled to −30° C, and to the resultant was added phosphorus pentachloride (1.8 parts), followed by stirring at −20° to −15° C for one hour.

To the resultant was added thioacetamide (1.0 part) and stirred at −10° to −15° C for one hour, followed by addition of methanol (20 volume parts). And then sulfur monochloride (1.0 volume part) was added and stirred for ten minutes, and then, to the resultant water (10 volume parts) was added. The mixture was adjusted to pH 3.3 with ammonium bicarbonate, followed by cooling with ice for one hour. The resultant crystals were recovered by filtration, washed with 50 % methanol, methanol and dichloromethane in this order and dried to give 7-amino-3-[5-(β-hydroxyethylthio)-1,3,4-thiadiazol-2-yl]thiomethyl-3-cephem-4-carboxylic acid (1.3 parts). IR (KBr disc): 1800 cm$^{-1}$ NMR(in D$_2$O and NaHCO$_3$): δ 3.54(t,j=6Hz,SCH$_2$CH$_2$-), 3.54 and 3.73 (q,J=16Hz,2-CH$_2$-), 3.91(t,J=6Hz,CH$_2$OH), 4.07 and 4.38(q,J=13Hz,3-CH$_2$), 5.05(d,J=5Hz,6-H), 5.45(d,J=5Hz,7-H).

EXAMPLE 24

According to the similar procedure to that of Example 23-(2), from the following 7-substituted amino-3-cephem-4-carboxylic acid derivatives (i.e. starting compounds) were obtained the corresponding 7-amino-3-cephem-4-carboxylic acid derivatives (i.e. products) respectively, which are described in the following table;

| Ex. | Starting compound (amount used) | Product (yield) | IR: cm$^{-1}$ (KBr disc) | NMR: δ |
|---|---|---|---|---|
| 24-(1) | 7-(D-5-phthalimido-5-carboxy valeramido)-3-(5-carboxy-methyl-1,3,4-thiadiazol-2-yl) thiomethyl-3-cephem-4-carboxylic acid | 7-amino-3-(5-carboxy-methyl-1,3,4-thiadiazol-2-yl)thiomethyl-3-cephem-4-carboxylic acid | | (100MHz, in NaHCO$_3$—D$_2$O); 3.60, 3.98(ABq,J = 18Hz, 2-CH$_2$), 3.98(s,CH$_2$COO), 4.23,4.67(ABq,J = 14Hz, 3-CH$_2$),5.25(d,J = 5Hz,6-H), |

| Ex. | Starting compound (amount used) | Product (yield) | IR: cm$^{-1}$ (KBr disc) | NMR: δ |
|---|---|---|---|---|
| | (3.3 parts) | (1.3 parts) | 1800 | 5.64(d,J = 5Hz,7-H) |
| 24-(2) | 7-(D-5-phthalimido-5-carboxy-valeramido)-3-[5-(N,N-dimethylcarbamoylmethyl)-1,3,4-thiadiazol-2-yl]thiomethyl-3-cephem-4-carboxylic acid (3.4 parts) | 7-amino-3-[5-(N,N-dimethylcarbamoyl-methyl)-1,3,4-thia-diazol-2-yl]thio-methyl-3-cephem-4-carboxylic acid (1.4 parts) | 1795 1642 | (60MHz, in NaHCO$_3$—D$_2$O); 3.00,3.5(each s,N(CH$_3$)$_2$), 3.36,3.78(ABq,J = 17Hz,2-CH$_2$),3.99,4.45(Abq,J = 13Hz, 3-CH$_2$),4.10(s,—CH$_2$CO), 5.06(d,J = 5Hz,6-H),5.44 (d,J = 5Hz,7-H) |

What we claim is:

1. A process for preparing a compound of the formula

H$_2$N-A wherein A is a penicillin moiety represented by the formula

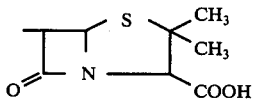

wherein the carboxy group is unprotected or protected by a conventional protecting group, or A is a cephalosporin moiety represented by the formula

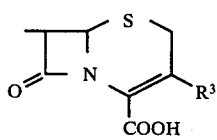

wherein the carboxy group is unprotected or protected by a conventional protecting group and R$^3$ is a group which does not take part in the reaction described below and is a member selected from the group consisting of 1. lower alkyl,
2. lower alkoxymethyl,
3. lower alkanoyloxymethyl,
4. a group represented by the formula

-CH$_2$SR$^4$ wherein R$^4$ is lower alkyl or a 5 or 6 membered nitrogen-containing heterocyclic group having 1 to 4 hetero atoms selected from the group consisting of nitrogen, oxygen and sulfur, the nitrogen being in the oxide or non-oxide form, which nitrogen-containing heterocyclic group is unsubstituted or substituted by (a) lower alkyl, (b) trifluoromethyl, (c) lower alkoxy, (d) halogen, (e) amino, (f) mercapto, (g) hydroxy, (h) carbamoyl, (i) carboxy, (j) lower alkyl substituted by hydroxy, mercapto, amino, morpholino, carboxy, sulfo, carbamoyl, alkoxycarbonyl having 2 to 13 carbon atoms, mono- or di- lower alkyl carbamoyl, alkoxy having 1 to 12 carbon atoms, alkylthio having 1 to 3 carbon atoms, alkylsulfonyl having 1 to 3 carbon atoms, acyloxy selected from the group consisting of acetoxy, propionyloxy, valeryloxy, caproyloxy, benzoyloxy and phenylacetoxy, morpholinocarbonyl or N-lower alkylamino, (k) mercapto substituted by lower alkyl wherein the lower alkyl is unsubstituted or substituted by hydroxy, mercapto, amino, morpholino, carboxy, sulfo, carbamoyl, alkoxycarbonyl having 2 to 13 carbon atoms, mono- or di- lower alkyl carbamoyl, alkoxy having 1 to 12 carbon atoms, alkylthio having 1 to 3 carbon atoms, alkylsulfonyl having 1 to 3 carbon atoms, acyloxy selected from the group consisting of acetoxy, propionyloxy, valeryloxy, caproyloxy, benzoyloxy and phenylacetoxy, morpholinocarbonyl or N-lower alkylamino, or (l) amino mono- or di- substituted by carboxy, carbamoyl, lower alkyl, alkoxycarbonyl having 2 to 13 carbon atoms, lower alkyl carbamoyl, or lower alkyl substituted by hydroxy, mercapto, amino, morpholino, carboxy, sulfo, carbamoyl, alkoxycarbonyl having 2 to 13 carbon atoms, mono- or di-lower alkyl carbamoyl, alkoxy having 1 to 12 carbon atoms, alkylthio having 1 to 3 carbon atoms, alkylsulfonyl having 1 to 3 carbon atoms, acyloxy selected from the group consisting of acetoxy, propionyloxy, valeryloxy, caproyloxy, benzoyloxy and phenylacetoxy, morpholinocarbonyl or N-lower alkylamino, and 5. an iminomethyl group of the formula

-CH=NOR$^5$ wherein R$^5$ is alkyl having 1 to 6 carbon atoms or cycloalkyl having up to 6 carbon atoms, which alkyl and cycloalkyl groups are unsubstituted or substituted by (a) allyl, (b) phenyl, (c) an unsubstituted 5 or 6 membered heterocyclic group having 1 or 2 hetero atoms selected from the group consisting of nitrogen, oxygen and sulfur, (d) carboxy or (e) pyridinium, which comprises reacting a compound of the formula

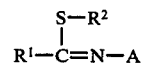

wherein A has the same meaning as above, R$^1$ is an organic residue derived from an acylamido group in the 6-position of a penicillin or the 7- position of a cephalosporin by eliminating the -CONH- moiety of the acylamido group, which organic residue is capable of combination with a thiocarbonyl group to form a thioacyl group, and R$^2$ is a member selected from the group consisting of (1) lower alkoxycarbonylthio, (2) halocarbonylthio wherein the halo is chloro or bromo, (3) lower alkylthio, (4) mono-, di- or tri-halo lower alkylthio wherein the halo is chloro or bromo, (5) mono- or di- lower alkylaminothio, (6) mercapto substituted by an unsubstituted nitrogen-containing 5 or 6 membered heterocyclic group, (7) halothio wherein the halo is chloro or bromo and (8) halodithio wherein the halo is chloro or bromo, with a solvolysis solvent selected from the group consisting of aliphatic alcohols having 1 to 4 carbon atoms, glycols having 2 to 4 carbon atoms, glycerine, acetic acid, propionic acid, methylmercaptan, ethylmercaptan and water.

2. A process for preparing a compound of the formula

H$_2$N-A wherein A is a penicillin moiety represented by the formula

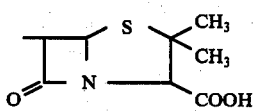

wherein the carboxy group is unprotected or protected by a conventional protecting group, or A is a cephalosporin moiety represented by the formula

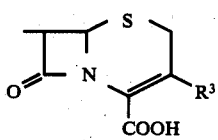

wherein the carboxy group is unprotected or protected by a conventional protecting group and $R^3$ is a group which does not take part in the reactions described below and is a member selected from the group consisting of
1. lower alkyl,
2. lower alkoxymethyl,
3. lower alkanoyloxymethyl,
4. a group represented by the formula

-CH$_2$SR$^4$ wherein $R^4$ is lower alkyl or a 5 or 6 membered nitrogen-containing heterocyclic group having 1 to 4 hetero atoms selected from the group consisting of nitrogen, oxygen and sulfur, the nitrogen being in the oxide or non-oxide form, which nitrogen-containing heterocyclic group is unsubstituted or substituted by (a) lower alkyl, (b) trifluoromethyl, (c) lower alkoxy, (d) chlorine or bromine, (e) amino, (f) mercapto, (g) hydroxy, (h) carbamoyl, (i) carboxy, (j) lower alkyl substituted by hydroxy, mercapto, amino, morpholino, carboxy, sulfo, carbamoyl, alkoxycarbonyl having 2 to 13 carbon atoms, mono- or di-lower alkyl carbamoyl, alkoxy having 1 to 12 carbon atoms, alkylthio having 1 to 3 carbon atoms, alkylsulfonyl having 1 to 3 carbon atoms, acyloxy selected from the group consisting of acetoxy, propionyloxy, valeryloxy, caproyloxy, benzoyloxy and phenylacetoxy, morpholinocarbonyl or N-lower alkylamino, (k) mercapto substituted by lower alkyl wherein the lower alkyl is unsubstituted or substituted by hydroxy, mercapto, amino, morpholino, carboxy, sulfo, carbamoyl, alkoxycarbonyl having 2 to 13 carbon atoms, mono- or di- lower alkyl carbamoyl, alkoxy having 1 to 12 carbon atoms, alkylthio having 1 to 3 carbon atoms, alkylsulfonyl having 1 to 3 carbon atoms, acyloxy selected from the group consisting of acetoxy, propionyloxy, valeryloxy, caproyloxy, benzoyloxy and phenylacetoxy, morpholinocarbonyl or N-lower alkylamino, or (1) amino mono- or di- substituted by carboxy, carbamoyl, lower alkyl, alkoxycarbonyl having 2 to 13 carbon atoms, lower alkyl carbamoyl, or lower alkyl substituted by hydroxy, mercapto, amino, morpholino, carboxy, sulfo, carbamoyl, alkoxycarbonyl having 2 to 13 carbon atoms, mono- or di- lower alkyl carbamoyl, alkoxy having 1 to 12 carbon atoms, alkylthio having 1 to 3 carbon atoms, alkylsulfonyl having 1 to 3 carbon atoms, acyloxy selected from the group consisting of acetoxy, propionyloxy, valeryloxy, caproyloxy, benzoyloxy and phenylacetoxy, morpholinocarbonyl or N-lower alkylamino, and
5. an iminomethyl group of the formula

-CH=NOR$^5$ wherein $R^5$ is alkyl having 1 to 6 carbon atoms or cycloalkyl having up to 6 carbon atoms, which alkyl and cycloalkyl groups are unsubstituted or substituted by (a) allyl, (b) phenyl, (c) an unsubstituted 5 or 6 membered heterocyclic group having 1 or 2 hetero atoms selected from the group consisting of nitrogen, oxygen and sulfur, (d) carboxy or (e) pyridinium,
which comprises reacting a compound of the formula

wherein $R^1$ is an organic residue derived from an acylamido group in the 6- position of a penicillin or the 7- position of a cephalosporin by eliminating the -CONH- moiety of the acylamido group, which organic residue is capable of combination with a thiocarbonyl group to form a thioacyl group, and A has the same meaning as above,
with a disulfidizing agent selected from the group consisting of (1) sulfenyl halides of the formula

R$^2$X wherein $R^2$ is (a) lower alkoxycarbonylthio, (b) halocarbonylthio wherein the halo is chloro or bromo, (c) lower alkylthio, (d) mono-, di- or tri-halo lower alkylthio wherein the halo is chloro or bromo, (e) mono- or di- lower alkylaminothio, (f) mercapto substituted by an unsubstituted nitrogen-containing 5 or 6 membered heterocyclic group, (g) halothio wherein the halo is chloro or bromo or (h) halodithio wherein the halo is chloro or bromo, and X is chlorine or bromine, (2) isothioureas of the formula

wherein $R^2$ has the same meaning as above, (3) imides of the formula

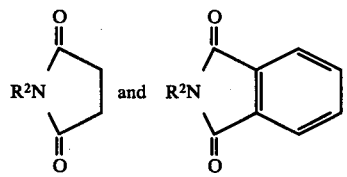

wherein $R^2$ has the same meaning as above, and (4) Bunte salts of the formula

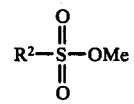

wherein $R^2$ has the same meaning as above and Me represents alkali metal,
to obtain a disulfide compound of the formula

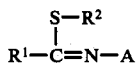

wherein $R^1$, $R^2$ and A have the same meanings as above, and reacting the disulfide compound with a solvolysis solvent selected from the group consisting of aliphatic alcohols having 1 to 4 carbon atoms, glycols having 2 to 4 carbon atoms, glycerine, acetic acid, propionic acid, methylmercaptan, ethylmercaptan and water.

3. A process for preparing a compound of the formula
$H_2N-A$
wherein A is a penicillin moiety represented by the formula

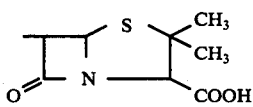

wherein the carboxy group is unprotected or protected by a conventional protecting group, or A is a cephalosporin moiety represented by the formula

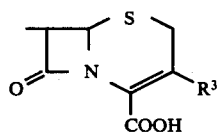

wherein the carboxy group is unprotected or protected by a conventional protecting group and $R^3$ is a group which does not take part in the reaction described below and is a member selected from the group consisting of
 1. lower alkyl,
 2. lower alkoxymethyl,
 3. lower alkanoyloxymethyl,
 4. a group represented by the formula

wherein $R^4$ is lower alkyl or a 5 or 6 membered nitrogen-containing heterocyclic group having 1 to 4 hetero atoms selected from the group consisting of nitrogen, oxygen and sulfur, the nitrogen being in the oxide or non-oxide form, which nitrogen-containing heterocyclic group is unsubstituted or substituted by (a) lower alkyl, (b) trifluoromethyl, (c) lower alkoxy, (d) halogen, (e) amino, (f) mercapto, (g) hydroxy, (h) carbamoyl, (i) carboxy, (j) lower alkyl substituted by hydroxy, mercapto, amino, morpholino, carboxy, sulfo, carbamoyl, alkoxycarbonyl selected from the group consisting of methoxycarbonyl, ethoxycarbonyl, propoxycarbonyl, butoxycarbonyl, isobutoxycarbonyl, hexyloxycarbonyl, octyloxycarbonyl, decyloxycarbonyl and dodecyloxycarbonyl, mono- or di- lower alkyl carbamoyl, alkoxy selected from the group consisting of methoxy, ethoxy, propoxy, butoxy, isobutoxy, hexyloxy, octyloxy, decyloxy and dodecyloxy, alkylthio selected from the group consisting of methylthio, ethylthio and isopropylthio, alkylsulfonyl selected from the group consisting of methylsulfonyl, ethylsulfonyl and isopropylsulfonyl, acyloxy selected from the group consisting of acetoxy, propionyloxy, valeryloxy, caproyloxy, benzoyloxy and phenylacetoxy, morpholinocarbonyl or N-lower alkylamino, (k) mercapto substituted by lower alkyl wherein the lower alkyl is unsubstituted or substituted by hydroxy, mercapto, amino, morpholino, carboxy, sulfo, carbamoyl, alkoxycarbonyl selected from the group consisting of methoxycarbonyl, ethoxycarbonyl, propoxycarbonyl, butoxycarbonyl, isobutoxycarbonyl, hexyloxycarbonyl, octyloxycarbonyl, decyloxycarbonyl and dodecyloxycarbonyl, mono- or di- lower alkyl carbamoyl, alkoxy selected from the group consisting of methoxy, ethoxy, propoxy, butoxy, isobutoxy, hexyloxy, octyloxy, decyloxy and dodecyloxy, alkylthio selected from the group consisting of methylthio, ethylthio and isopropylthio, alkylsulfonyl selected from the group consisting of methylsulfonyl, ethylsulfonyl and isopropylsulfonyl, acyloxy selected from the group consisting of acetoxy, propionyloxy, valeryloxy, caproyloxy, benzoyloxy and phenylacetoxy, morpholinocarbonyl or N-lower alkylamino, or (1) amino mono- or di- substituted by carboxy, carbamoyl, lower alkyl, alkoxycarbonyl selected from the group consisting of methoxycarbonyl, ethoxycarbonyl, propoxycarbonyl, butoxycarbonyl, isobutoxycarbonyl, hexyloxycarbonyl, octyloxycarbonyl, decyloxycarbonyl and dodecyloxycarbonyl, lower alkyl carbamoyl, or lower alkyl substituted by hydroxy, mercapto, amino, morpholino, carboxy, sulfo, carbamoyl, alkoxycarbonyl selected from the group consisting of methoxycarbonyl, ethoxycarbonyl, propoxycarbonyl, butoxycarbonyl, isobutoxycarbonyl, hexyloxycarbonyl, octyloxycarbonyl, decyloxycarbonyl and dodecyloxycarbonyl, mono- or di- lower alkyl carbamoyl, alkoxy selected from the group consisting of methoxy, ethoxy, propoxy, butoxy, isobutoxy, hexyloxy, octyloxy, decyloxy and dodecyloxy, alkylthio selected from the group consisting of methylthio, ethylthio and isopropylthio, alkylsulfonyl selected from the group consisting of methylsulfonyl, ethylsulfonyl and isopropylsulfonyl, acyloxy selected from the group consisting of acetoxy, propionyloxy, valeryoxy, caproyloxy, benzoyloxy and phenylacetoxy, morpholinocarbonyl or N-lower alkylamino, and
 5. an iminomethyl group of the formula

wherein $R^5$ is alkyl having 1 to 6 carbon atoms or cycloalkyl having up to 6 carbon atoms, which alkyl and cycloalkyl groups are unsubstituted or substituted by (a) allyl, (b) phenyl, (c) an unsubstituted 5 or 6 membered heterocyclic group having 1 or 2 hetero atoms selected from the group consisting of nitrogen, oxygen and sulfur, (d) carboxy or (e) pyridinium, which comprises reacting a compound of the formula

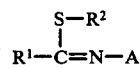

wherein A has the same meaning as above, $R^1$ is an organic residue derived from an acylamido group in the 6- position of a penicillin or the 7- position of a cephalosporin by eliminating the -CONH- moiety of the acylamido group, which organic residue is capable of combination with a thiocarbonyl group to form a thioacyl group, and $R^2$ is a member selected from the group consisting of (1) lower alkoxycarbonylthio, (2) halocarbonylthio wherein the halo is chloro or bromo, (3) lower alkylthio, (4) mono-, di- or tri-halo lower alkylthio wherein the halo is chloro or bromo, (5) mono- or di- lower alkylamino thio, (6) mercapto substituted by an unsubstituted nitrogen containing 5 or 6 membered heterocyclic group, (7) halothio wherein the halo is chloro or bromo and (8) halodithio wherein the halo is chloro or bromo, with a solvolysis solvent selected from the group consisting of aliphatic alcohols having 1 to 4 carbon atoms, ethylene glycol, propylene glycol, 1,3-butanediol, glycerine, acetic acid, propionic acid, methylmercaptan, ethylmercaptan and water.

4. A process for preparing a compound of the formula

wherein A is a penicillin moiety represented by the formula

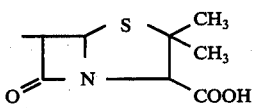

wherein the carboxy group is unprotected or protected by a conventional protecting group, or A is a cephalosporin moiety represented by the formula

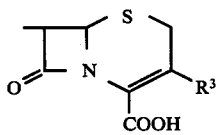

wherein the carboxy group is unprotected or protected by a conventional protecting group and $R^3$ is a group which does not take part in the reactions described below and is a member selected from the group consisting of
 1. lower alkyl,
 2. lower alkoxymethyl,
 3. lower alkanoyloxymethyl,
 4. a group represented by the formula

wherein $R^4$ is lower alkyl or a 5 or 6 membered nitrogen-containing heterocyclic group having 1 to 4 hetero atoms selected from the group consisting of nitrogen, oxygen and sulfur, the nitrogen being in the oxide or non-oxide form, which nitrogen-containing heterocyclic group is unsubstituted or substituted by (a) lower alkyl, (b) trifluoromethyl, (c) lower alkoxy, (d) chlorine or bromine, (e) amino, (f) mercapto, (g) hydroxy, (h) carbamoyl, (i) carboxy, (j) lower alkyl substituted by hydroxy, mercapto, amino, morpholino, carboxy, sulfo, carbamoyl, alkoxycarbonyl selected from the group consisting of methoxycarbonyl, ethoxycarbonyl, propoxycarbonyl, butoxycarbonyl, isobutoxycarbonyl, hexyloxycarbonyl, octyloxycarbonyl, decyloxycarbonyl and dodecyloxycarbonyl, mono- or di- lower alkyl carbamoyl, alkoxy selected from the group consisting of methoxy, ethoxy, propoxy, butoxy, isobutoxy, hexyloxy, octyloxy, decyloxy and dodecyloxy, alkylthio selected from the group consisting of methylthio, ethylthio and isopropylthio, alkylsulfonyl selected from the group consisting of methylsulfonyl, ethylsulfonyl and isopropylsulfonyl, acyloxy selected from the group consisting of acetoxy, propionyloxy, valeryloxy, caproyloxy, benzoyloxy and phenylacetoxy, morpholinocarbonyl or N-lower alkylamino, (k) mercapto substituted by lower alkyl wherein the lower alkyl is unsubstituted or substituted by hydroxy, mercapto, amino, morpholino, carboxy, sulfo, carbamoyl, alkoxycarbonyl selected from the group consisting of methoxycarbonyl, ethoxycarbonyl, propoxycarbonyl, butoxycarbonyl, isobutoxycarbonyl, hexyloxycarbonyl, octyloxycarbonyl, decyloxycarbonyl and dodecyloxycarbonyl, mono- or di- lower alkyl carbamoyl, alkoxy selected from the group consisting of methoxy, ethoxy, propoxy, butoxy, isobutoxy, hexyloxy, octyloxy, decyloxy and dodecyloxy, alkylthio selected from the group consisting of methylthio, ethylthio and isopropylthio, alkylsulfonyl selected from the group consisting of methylsulfonyl, ethylsulfonyl and isopropylsulfonyl, acyloxy selected from the group consisting of acetoxy, propionyloxy, valeryloxy, caproyloxy, benzoyloxy and phenylacetoxy, morpholinocarbonyl or N-lower alkylamino, or (1) amino mono- or di- substituted by carboxy, carbamoyl, lower alkyl, alkoxycarbonyl selected from the group consisting of methoxycarbonyl, ethoxycarbonyl, propoxycarbonyl, butoxycarbonyl, isobutoxycarbonyl, hexyloxycarbonyl, octyloxycarbonyl, decyloxycarbonyl and dodecyloxycarbonyl, lower alkyl carbamoyl, or lower alkyl substituted by hydroxy, mercapto, amino, morpholino, carboxy, sulfo, carbamoyl, alkoxycarbonyl selected from the group consisting of methoxycarbonyl, ethoxycarbonyl, propoxycarbonyl, butoxycarbonyl, isobutoxycarbonyl, hexyloxycarbonyl, octyloxycarbonyl, decyloxycarbonyl and dodecyloxycarbonyl, mono- or di- lower alkyl carbamoyl, alkoxy selected from the group consisting of methoxy, ethoxy, propoxy, butoxy, isobutoxy, hexyloxy, octyloxy, decyloxy and dodecyloxy, alkylthio selected from the group consisting of methylthio, ethylthio and isopropylthio, alkylsulfonyl selected from the group consisting of methylsulfonyl, ethylsulfonyl and isopropylsulfonyl, acyloxy selected from the group consisting of acetoxy, propionyloxy, valeryloxy, caproyloxy, benzoyloxy and phenylacetoxy, morpholinocarbonyl or N-lower alkylamino, and
 5. an iminomethyl group of the formula

wherein $R^5$ is alkyl having 1 to 6 carbon atoms or cycloalkyl having up to 6 carbon atoms, which alkyl and cycloalkyl groups are unsubstituted or substituted by (a) allyl, (b) phenyl, (c) an unsubstituted 5 or 6 membered heterocyclic group having 1 or 2 hetero atoms selected from the group consisting of nitrogen, oxygen and sulfur, (d) carboxy or (e) pyridinium, which comprises reacting a compound of the formula

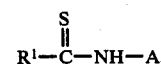

wherein $R^1$ is an organic residue derived from an acylamido group in the 6- position of a penicillin or the 7- position of a cephalosporin by eliminating the -CONH- moiety of the acylamido group, which organic residue is capable of combination with a thiocarbonyl group to form a thioacyl group, and A has the same meaning as above, with a disulfidizing agent selected from the group consisting of (1) sulfenyl halides of the formula

R²X wherein R² is (a) lower alkoxycarbonylthio, (b) halocarbonylthio wherein the halo is chloro or bromo, (c) lower alkylthio, (d) mono-, di- or tri-halo lower alkylthio wherein the halo is chloro or bromo, (e) mono- or di- lower alkylaminothio, (f) mercapto substituted by an unsubstituted nitrogen-containing 5 or 6 membered heterocyclic group, (g) halothio wherein the halo is chloro or bromo or (h) halodithio wherein the halo is chloro or bromo, and X is chlorine or bromine, (2) isothioureas of the formula

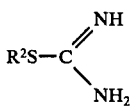

wherein R² has the same meaning as above, (3) imides of the formula

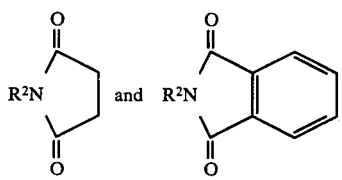

wherein R² has the same meaning as above, and (4) Bunte salts of the formula

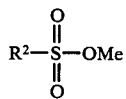

wherein R² has the same meaning as above and Me represents alkali metal,
to obtain a disulfide compound of the formula

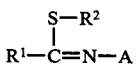

wherein R¹, R² and A have the same meanings as above, and
reacting the disulfide compound with a solvolysis solvent selected from the group consisting of aliphatic alcohols having 1 to 4 carbon atoms, ethylene glycol, propylene glycol, 1,3-butanediol, glycerine, acetic acid, propionic acid, methylmercaptan, ethylmercaptan and water.

5. A process as claimed in claim 1, wherein the lower alkanoyloxymethyl is acetoxymethyl or propionyloxymethyl.

6. A process as claimed in claim 1, wherein the mono-, di- or tri-halo lower alkylthio is monochloromethylthio, dichloromethylthio, trichloromethylthio or tribromomethylthio.

7. A process as claimed in claim 2, wherein the lower alkanoyloxymethyl is acetoxymethyl or propionyloxymethyl.

8. A process as claimed in claim 2, wherein the mono-, di- or tri-halo lower alkylthio is monochloromethylthio, dichloromethylthio, trichloromethylthio or tribromomethylthio.

9. A process as claimed in claim 3, wherein the lower alkanoyloxymethyl is acetoxymethyl or propionyloxymethyl.

10. A process as claimed in claim 3, wherein the mono-, di- or tri-halo lower alkylthio is monochloromethylthio, dichloromethylthio, trichloromethylthio or tribromomethylthio.

11. A process as claimed in claim 4, wherein the lower alkanoyloxymethyl is acetoxymethyl or propionyloxymethyl.

12. A process as claimed in claim 4, wherein the mono-, di- or tri-halo lower alkylthio is monochloromethylthio, dichloromethylthio, trichloromethylthio or tribromomethylthio.

13. A process as claimed in claim 2, wherein the halothio is chlorothio; the halodithio is chlorodithio; the lower alkoxycarbonylthio is methoxycarbonylthio; the halocarbonylthio is chlorocarbonylthio; the lower alkylthio is methylthio, ethylthio, propylthio, isopropylthio, butylthio or isobutylthio; the mono-, di- or trihalo-loweralkylthio is monochloromethylthio, dichloromethylthio, trichloromethylthio or tribromomethylthio; the mono- or diloweralkylaminothio is methylaminothio, dimethylaminothio or diethylaminothio and the nitrogen-containing 5 to 6 membered heterocyclic group is morpholinothio.

14. A process as claimed in claim 13, wherein the disulfidizing agent is Cl₃CSCl, ClCH₂SCl, CH₃OCOSCl, ClCOSCl, CH₃SCl, Cl₃CSSCl, (C₂H₅)₂NSCl,

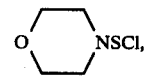

S-methylthioisothiourea, S-isobutylthioisothiourea, N-methylthiosuccinimide, N-isopropylthiosuccinimide, N-ethylthiophthalimide, N-n-butylthiophthalimide, N-propylthiophthalimide, sulfur chloride or sulfur dichloride.

15. A process as claimed in claim 2, wherein A is the penicillin moiety as defined in claim 2.

16. A process as claimed in claim 2, wherein A is the cephalosporin moiety as defined in claim 2.

17. A process as claimed in claim 1, wherein the solvolysis solvent is a straight chain monohydric alcohol having 1 to 3 carbon atoms.

18. A process as claimed in claim 17, wherein the straight chain monohydric alcohol is methanol.

19. A process as claimed in claim 1, wherein R¹ is a member selected from the group consisting of phenyl, thienylmethyl, phenoxymethyl, benzyl and 4-amino-4-carboxybutyl whose amino and/or carboxy group is unprotected or protected by a conventional protecting group.

20. A process as claimed in claim 19, wherein the protective group for the amino group of the 4-amino-4-carboxybutyl group is a member selected from the group consisting of phthaloyl, isobornyloxycarbonyl, p-(t-butyl)benzoyl and p-(t-butyl)benzenesulfonyl.

21. A process as claimed in claim 20, wherein the protective group for the carboxy group of the 4-amino-4-carboxybutyl group is a member selected from the group consisting of β-methylsulfonyl ethyl, dimethylsilyl, trimethylsilyl and phosphorous trichloride.

22. A process as claimed in claim 1, wherein A is the cephalosporin moiety.

23. A process as claimed in claim 22, wherein $R^3$ is a group represented by the formula

wherein $R^4$ is a 5 to 6 membered nitrogen-containing heterocyclic group having 1 to 4 hetero atoms selected from the group consisting of nitrogen, oxygen and sulfur, which is unsubstituted or substituted by alkyl having 1 to 4 carbon atoms, the nitrogen being in the oxide or non-oxide form.

24. A process as claimed in claim 23, wherein the nitrogen-containing heterocyclic group is a member selected from the group consisting of pyridyl, N-oxido-pyridyl, pyrimidyl, pyridazinyl, N-oxido-pyridazinyl, pyrazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl and 2H-tetrazolyl.

25. A process as claimed in claim 23, wherein $R^3$ is a member selected from the group consisting of (1-methyltetrazol-5-yl)thiomethyl, (5-methyl-1,3,4-thiadiazol-2-yl)thiomethyl, (1,3,4-thiadiazol-2-yl)thiomethyl and (5-methyl-1,3,4-oxadiazol-2-yl)thiomethyl.

26. A process as claimed in claim 22, wherein in the starting compound $R^1$ is 4-t-butylbenzoylamido-4-carboxybutyl, $R^2$ is chlorodithio, $R^3$ is (1-methyltetrazol-5-yl)thiomethyl and each carboxy group is protected with a dimethylsilyl group.

27. A process as claimed in claim 22, wherein in the starting compound $R^1$ is 4-phthalimido-4-carboxybutyl, $R^2$ is chlorodithio, $R^3$ is (1-methyltetrazol-5-yl)thiomethyl and each carboxy group is protected with a dimethylsilyl group.

28. A process as claimed in claim 22, wherein in the starting compound $R^1$ is 4-t-butylbenzenesulfonamido-4-carboxybutyl, $R^2$ is chlorodithio, $R^3$ is (1-methyltetrazol-5-yl)thiomethyl and each carboxy group is protected with a dimethylsilyl group.

29. A process as claimed in claim 22, wherein in the starting compound $R^1$ is 4-benzoylamido-4-carboxybutyl, $R^2$ is chlorodithio, $R^3$ is (1-methyltetrazol-5-yl)thiomethyl and each carboxy group is protected with a dimethylsilyl group.

30. A process as claimed in claim 22, wherein in the starting compound $R^1$ is 4-isobornyloxycarbonylamido-4-carboxybutyl, $R^2$ is chlorodithio, $R^3$ is (1-methyltetrazol-5-yl)thiomethyl and each carboxy group is protected with a dimethylsilyl group.

31. A process as claimed in claim 22, wherein in the starting compound $R^1$ is 4-phthalimido-4-carboxybutyl, $R^2$ is chlorodithio, $R^3$ is (5-methyl-1,3,4-thiadiazol-2-yl)thiomethyl and each carboxy group is protected with a dimethylsilyl group.

32. A process as claimed in claim 22, wherein in the starting compound $R^1$ is 4-phthalimido-4-carboxybutyl, $R^2$ is chlorodithio, $R^3$ is (1,3,4-thiadiazol-2-yl)thiomethyl and each carboxy group is protected with a dimethylsilyl group.

33. A process as claimed in claim 22, wherein in the starting compound $R^1$ is 4-phthalimido-4-carboxybutyl, $R^2$ is chlorodithio, $R^3$ is (5-methyl-1,3,4-oxadiazol-2-yl)thiomethyl and each carboxy group is protected with a dimethylsilyl group.

34. A process as claimed in claim 22, wherein in the starting compound $R^1$ is benzyl, $R^2$ is chlorodithio, $R^3$ is methyl and the carboxy group is protected with a β-methylsulfonylethyl group.

35. A process as claimed in claim 22, wherein in the starting compound $R^1$ is benzyl, $R^2$ is trichloromethylthio, $R^3$ is methyl and the carboxy group is protected with a β-methylsulfonylethyl group.

36. A process as claimed in claim 22, wherein in the starting compound $R^1$ is 4-phthalimido-4-carboxybutyl, $R^2$ is chlorodithio, $R^3$ is [5-(β-hydroxyethylthio)-1,3,4-thiadiazol-2-yl]thiomethyl and each carboxy group is protected with a dimethylsilyl group.

37. A process as claimed in claim 22, wherein in the starting compound $R^1$ is 4-phthalimido-4-carboxybutyl, $R^2$ is chlorodithio, $R^3$ is (5-carboxymethyl-1,3,4-thiadiazol-2-yl)-thiomethyl and each carboxy group is protected with a dimethylsilyl group.

38. A process as claimed in claim 22, wherein in the starting compound $R^1$ is 4-phthalimido-4-carboxybutyl, $R^2$ is chlorodithio, $R^3$ is [5-(N,N-dimethylcarbamoylmethyl)-1,3,4-thiadiazol-2-yl]thiomethyl and each carboxy group is protected with a dimethylsilyl group.

39. A process as claimed in claim 22, wherein in the starting compound $R^1$ is 4-phthalimido-4-carboxybutyl, $R^2$ is trichloromethylthio, $R^3$ is acetoxymethyl and each carboxy group is protected with a dimethylsilyl group.

40. A process according to claim 2, wherein 7-amino-3-(1-methyltetrazol-5-yl)thiomethyl-3-cephem-4-carboxylic acid is produced by reacting 7-(D-5-p-t-butylbenzoylamido-5-carboxyvalerthioamido)-3-(1-methyltetrazol-5-yl)thiomethyl-3-cephem-4-carboxylic acid, whose carboxy groups are protected with dimethylsilyl, with sulfur monochloride, and reacting the resultant compound with methanol.

41. A process according to claim 2, wherein 7-amino-3-(5-methyl-1,3,4-thiadiazol-2-yl)thiomethyl-3-cephem-4-carboxylic acid is produced by reacting 7-(D-5-phthalimido-5-carboxyvalerthioamido)-3-(5-methyl-1,3,4-thiadiazol-2-yl)thiomethyl-3-cephem-4-carboxylic acid, whose carboxy groups are protected with dimethylsilyl, with sulfur monochloride, and reacting the resultant compound with methanol.

42. A process according to claim 2, wherein 7-amino-3-(5-methyl-1,3,4-oxadiazol-2-yl)thiomethyl-3-cephem-4-carboxylic acid is produced by reacting 7-(D-5-phthalimido-5-carboxyvalerthioamido)-3-(5-methyl-1,3,4-oxadiazol-2-yl)thiomethyl-3-cephem-4-carboxylic acid, whose carboxy groups are protected with dimethylsilyl, with sulfur monochloride, and reacting the resultant compound with methanol.

43. A process according to claim 2, wherein 7-amino-3-(1,3,4-thiadiazol-2-yl)thiomethyl-3-cephem-4-carboxylic acid is produced by reacting 7-(D-5-phthalimido-5-carboxyvalerthioamido)-3-(1,3,4-thiadiazol-2-yl)thiomethyl-3-cephem-4-carboxylic acid, whose carboxy groups are protected with dimethylsilyl, with sulfur monochloride, and reacting the resultant compound with methanol.

44. A process according to claim 2, wherein 7-amino-3-(1-methyltetrazol-5-yl)thiomethyl-3-cephem-4-carboxylic acid is produced by reacting 7-(D-5-isobornyloxycarbonylamido-5-carboxyvalerthioamido)-3-(1-methyltetrazol-5-yl)thiomethyl-3-cephem-4-carboxylic acid, whose carboxy groups are protected by dimethylsilyl, with sulfur monochloride, and reacting the resultant compound with methanol.

45. A process according to claim 2, wherein 7-amino-3-(1-methyltetrazol-5-yl)thiomethyl-3-cephem-4-carboxylic acid is produced by reacting 7-(D-5- phthalimido-5-carboxyvalerthioamido)-3-(1-methyltetrazol-5-yl)thiomethyl-3-cephem-4-carboxylic acid, whose carboxy groups are protected with dimethylsilyl, with sulfur monochloride, and reacting the resultant compound with methanol.

46. A process according to claim 2, wherein 7-amino-3-(1-methyltetrazol-5-yl)thiomethyl-3-cephem-4-carboxylic acid is produced by reacting 7-(D-5-p-t-butylbenzenesulfonamido)-5-carboxyvalerthioamido)-3-(1-methyltetrazol-5-yl)thiomethyl-3-cephem-4-carboxylic acid, whose carboxy groups are protected by dimethylsilyl, with sulfur monochloride, and reacting the resultant compound with methanol.

47. A process according to claim 2, wherein 7-amino-3-(1-methyltetrazol-5-yl)thiomethyl-3-cephem-4-carboxylic acid is produced by reacting 7-(D-5-benzoylamido-5-carboxyvalerthioamido)-3-(1-methyltetrazol-5-yl)thiomethyl-3-cephem-4-carboxylic acid, whose carboxy groups are protected by dimethylsilyl, with sulfur monochloride, and reacting the resultant compound with methanol.

48. A process according to claim 2, wherein 7-amino-3-[5-($\beta$-hydroxyethylthio)-1,3,4-thiadiazol-2-yl]thiomethyl-3-cephem-4-carboxylic acid is produced by reacting 7-(D-5-phthalimido-5-carboxyvalerthioamido)-3-[5-($\beta$-hydroxyethylthio)-1,3,4-thiadiazol-2-yl]thiomethyl-3-cephem-4-carboxylic acid, whose carboxy groups are protected by dimethylsilyl, with sylfur monochloride, and reacting the resultant compound with methanol.

49. A process according to claim 2, wherein 7-amino-3-(5-carboxymethyl-1,3,4-thiadiazol-2-yl)thiomethyl-3-cephem-4-carboxylic acid is produced by reacting 7-(D-5-phthalimido-5-carboxyvalerthioamido)-3-(5-carboxymethyl-1,3,4-thiadiazol-2yl)thiomethyl-3-cephem-4carboxylic acid, whose carboxy groups are protected by dimethylsilyl, with sulfur monochloride, and reacting the resultant compound with methanol.

50. A process according to claim 2, wherein 7-amino-3-[5-(N,N-dimethylcarbamoylmethyl)-1,3,4-thiadiazol-2-yl]thiomethyl-3-cephem-4-carboxylic acid is produced by reacting 7-(D-5-phthalimido-5-carboxyvalerthioamido)-3-[5-(N,N-dimethylcarbamoylmethyl)-1,3,4-thiadiazol-2-yl]thiomethyl-3-cephem-4-carboxylic acid, whose carboxy groups are protected by dimethylsilyl, with sulfur monochloride, and reacting the resultant compound with methanol.

51. A process according to claim 2, wherein 7-aminocephalosporanic acid is produced by reacting 7(D-5-phthaloylimido-5carboxy valerthioamido)-3-acetoxymethyl-3-cephem-4-carboxylic acid, whose carboxy groups are protected by dimethylsilyl, with trichloromethanesulfenyl chloride, and reacting and resultant compound with methanol.

52. A process according to claim 2, wherein 7-aminocephalosporanic acid is produced by reacting 7-(D-5-phthaloylimido-5-carboxy valerthioamido)-3-acetoxymethyl-3- cephem-4-carboxylic acid, whose carboxy groups are protected by dimethylsilyl, with sulfur monochloride, and reacting the resultant compound with methanol.

53. A process according to claim 2, wherein $\beta$-methylsulfonylethyl 7-amino-3-desacetoxycephalosporanate is produced by reacting an adduct consisting of $\beta$-methylsulfonylethyl 7-phenylthioacetamido-3-desacetoxycephalosporanate, pyridine and hydrogen chloride with sulfur monochloride, and reacting the resultant compound with methanol.

54. A process according to claim 3, wherein the N-lower alkylamino is N,N-dimethylamino.

55. A process according to claim 4, wherein the N-lower alkylamino is N,N-dimethylamino.

* * * * *

UNITED STATES PATENT OFFICE
CERTIFICATE OF CORRECTION

Patent No. 4,068,071     Dated January 10, 1978

Inventor(s) Susumu Tsushima; Norichika Matsumoto and Mitsuo Numata

It is certified that error appears in the above-identified patent and that said Letters Patent are hereby corrected as shown below:

In the heading of the Patent under the section entitled "[30] Foreign Application Priority Data", change "48-3181" to --49-3181--.

Signed and Sealed this

Ninth Day of May 1978

[SEAL]

Attest:

RUTH C. MASON
Attesting Officer

LUTRELLE F. PARKER
Acting Commissioner of Patents and Trademarks